(12) United States Patent
Mihashi et al.

(10) Patent No.: US 7,241,012 B2
(45) Date of Patent: Jul. 10, 2007

(54) OPHTHALMOLOGIC APPARATUS

(75) Inventors: Toshifumi Mihashi, Tokyo (JP); Yoko Hirohara, Tokyo (JP); Teruhito Kuroda, Osaka (JP); Naoyuki Maeda, Osaka (JP); Takashi Fujikado, Osaka (JP)

(73) Assignee: Kabushiki Kaisha Topcon, Tokyo (JP)

( * ) Notice: Subject to any disclaimer, the term of this patent is extended or adjusted under 35 U.S.C. 154(b) by 723 days.

(21) Appl. No.: 10/758,285

(22) Filed: Jan. 16, 2004

(65) Prior Publication Data

US 2004/0212781 A1    Oct. 28, 2004

(30) Foreign Application Priority Data

Jan. 21, 2003  (JP) .............................. 2003-012819
Apr. 23, 2003  (JP) .............................. 2003-117730
Apr. 25, 2003  (JP) .............................. 2003-120967

(51) Int. Cl.
*A61B 3/10* (2006.01)
*A61B 3/00* (2006.01)

(52) U.S. Cl. ...................................... 351/212; 351/221
(58) Field of Classification Search ........ 351/200–208, 351/211, 212, 221–223, 237, 243
See application file for complete search history.

(56) References Cited

U.S. PATENT DOCUMENTS

| | | | |
|---|---|---|---|
| 5,054,907 A | 10/1991 | Sklar et al. | |
| 5,307,096 A | 4/1994 | Baroth et al. | |
| 5,341,180 A | * | 8/1994 | Isogai et al. ................. 351/206 |
| 6,022,108 A | * | 2/2000 | Yoshida et al. ............. 351/208 |
| 6,331,059 B1 | 12/2001 | Kudryashov et al. | |
| 6,447,119 B1 | 9/2002 | Stewart et al. | |

(Continued)

FOREIGN PATENT DOCUMENTS

EP    0 943 288 A1    9/1999

(Continued)

OTHER PUBLICATIONS

J. Nemeth et al., "High-speed videotopographic measurement of tear film build-up time", Invest. Ophthalmol. Vis. Sci., Jun. 2002, 43 (6):1783-90, abstract.

(Continued)

Primary Examiner—Hung Dang
Assistant Examiner—M. Hasan
(74) Attorney, Agent, or Firm—Foley & Lardner LLP

(57) ABSTRACT

There is provided an ophthalmologic apparatus which can be effectively used for the clinic of a dry eye by using, as a basic principle, that when a tear film dries up, a corneal shape is changed and/or a wavefront aberration becomes large. When a measurement is started, the ophthalmologic apparatus is aligned. An arithmetic part performs an initial setting of a measurement interval of the apparatus, a measurement time and the like by a wavefront measurement part. An input part or the arithmetic part triggers a measurement start, and the arithmetic part repeats a measurement of the corneal shape and corneal wavefront aberrations by a measurement part until time reaches a measurement end time. When the time reaches the measurement end time, a judgment part analyzes a breakup state as one index for judgment of a state of a dry eye. The judgment part obtains values relating to the breakup to output them, and performs an automatic diagnosis about dry eye on the basis of the values.

24 Claims, 22 Drawing Sheets

U.S. PATENT DOCUMENTS

2002/0163623 A1   11/2002   Hirohara et al.

FOREIGN PATENT DOCUMENTS

| EP | 1 437 084 A1 | 7/2004 |
| JP | 6-277179 A | 10/1994 |
| JP | 7-136120 A | 5/1995 |
| JP | 8-052112 A | 2/1996 |
| JP | 2002-125931 A | 5/2002 |
| WO | WO 03/053230 A1 | 7/2003 |
| WO | WO 03/063695 A1 | 8/2003 |

OTHER PUBLICATIONS

R. Rand et al., "Mathematical Model of a Placido Disk Keratometer and Its Implications for Recovery of Corneal Topography", Optometry and Vision Science, vol. 74, No. 11, Nov. 1997, pp. 926-930.

* cited by examiner $$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t) \\
\end{bmatrix}$$

FIG. 18

$$\begin{bmatrix}
i & 2j-i & \\
0 & 0 & 1 \\
1 & -1 & y \\
1 & 1 & x \\
2 & -2 & 2yx \\
2 & 0 & 2x^2 + 2y^2 - 1 \\
2 & 2 & x^2 - y^2 \\
3 & -3 & 3yx^2 - y^3 \\
3 & -1 & 3yx^2 + 3y^3 - 2y \\
3 & 1 & 3x^3 + 3xy^2 - 2x \\
3 & 3 & x^3 - 3xy^2 \\
4 & -4 & 4yx^3 - 4y^3 x \\
4 & -2 & 8yx^3 + 8y^3 x - 6yx \\
4 & 0 & 6x^4 + 12x^2 y^2 + 6y^4 - 6x^2 - 6y^2 + 1 \\
4 & 2 & 4x^4 - 4y^4 - 3x^2 + 3y^2 \\
4 & 4 & x^4 - 6x^2 y^2 + y^4 \\
5 & -5 & 5yx^4 - 10y^3 x^2 + y^5 \\
5 & -3 & 15yx^4 + 10y^3 x^2 - 5y^5 - 12yx^2 + 4y^3 \\
5 & -1 & 10yx^4 + 20y^3 x^2 + 10y^5 - 12yx^2 - 12y^3 + 3y \\
5 & 1 & 10x^5 + 20x^3 y^2 + 10xy^4 - 12x^3 - 12xy^2 + 3x \\
5 & 3 & 5x^5 - 10x^3 y^2 - 15xy^4 - 4x^3 + 12xy^2 \\
5 & 5 & x^5 - 10x^3 y^2 + 5xy^4 \\
6 & -6 & 6yx^5 - 20y^3 x^3 + 6y^5 x \\
6 & -4 & 24yx^5 - 24y^5 x - 20yx^3 + 20y^3 x \\
6 & -2 & 30yx^5 + 60y^3 x^3 + 30y^5 x - 40yx^3 - 40y^3 x + 12yx \\
6 & 0 & 20x^6 + 60x^4 y^2 + 60x^2 y^4 + 20y^6 - 30x^4 - 60x^2 y^2 - 30y^4 + 12x^2 + 12y^2 - 1 \\
6 & 2 & 15x^6 + 15x^4 y^2 - 15x^2 y^4 - 15y^6 - 20x^4 + 20y^4 + 6x^2 - 6y^2 \\
6 & 4 & 6x^6 - 30x^4 y^2 - 30x^2 y^4 + 6y^6 - 5x^4 + 30x^2 y^2 - 5y^4 \\
6 & 6 & x^6 - 15x^4 y^2 + 15x^2 y^4 - y^6
\end{bmatrix}$$

FIG. 19

FIFTH AND SIXTH ABERRATIONS

THIRD AND FOURTH ABERRATIONS $$\text{CORNEAL WAVEFRONT ABERRATION} = \begin{cases} -0.00418\,(t-5.927)+0.09299, & \text{for } t < 5.927, \\ 0.00458\,(t-5.927)+0.09299, & \text{for } t \geq 5.927. \end{cases}$$

OPHTHALMOLOGIC APPARATUS

BACKGROUND OF THE INVENTION

The present invention relates to an ophthalmologic apparatus, and particularly to an ophthalmologic apparatus for judging a state of a dry eye from the result of measurement of optical characteristics of a subject eye obtained by using a wavefront sensor.

Conventionally, as an ophthalmologic apparatus relating to a dry eye, techniques as described below can be enumerated.

Publication of unexamined patent application JP-A-6-277179 discloses an ophthalmologic measurement apparatus for quantitatively measuring fluorescence intensity from a cornea and a tear film of a subject eye in which a specified fluorescer is dropped. Publication of unexamined patent application JP-A-7-136120 discloses an ophthalmologic apparatus in which a color image of an interference pattern due to the interference of reflected lights of the front surface of a lipid layer and the back surface thereof is observed, so that the state of the lipid layer of the subject eye, the state of flow of tear fluid, and the like can be known, and a simple diagnosis of a local dry eye can be easily performed in a non-contact manner. Besides, publication of unexamined patent application JP-A-8-52112 discloses an ophthalmologic tear fluid observation apparatus in which only a signal light reflected from a tear film of a subject eye is incident on a CCD, so that vignetting does not occur in an observation visual field, and a clear tear fluid interference pattern without interfering light can be observed in the wide observation visual field.

However, it can not be necessarily said that the conventional ophthalmologic apparatus used in the clinic of the dry eye sufficiently satisfies requests relating to the judgment of the state of the dry eye.

SUMMARY OF THE INVENTION

In view of the above, an object of the invention is to provide an ophthalmologic apparatus which can be effectively used for the clinic of a dry eye by using, as a basic principle, that when a tear film dries up, a corneal shape is changed and/or a wavefront aberration becomes large. Further, another object of the invention is to provide an ophthalmologic apparatus which can take fatigue of an eye into consideration by counting blinks.

According to first solving means of the invention, there is provided an ophthalmologic apparatus comprising a first illuminating optical system for causing a measurement light flux with a specified shape to be incident on a cornea of a subject eye, a first light receiving optical system for receiving a reflected light from the cornea of the subject eye, a first light receiving part for changing a received reflected light from the first light receiving optical system into an electrical signal, a measurement part for obtaining a corneal shape of the subject eye from a received light. signal of the first light receiving part plural times at a measurement start point of time and during a subsequent specified period, and a judgment part for judging a state of a dry eye by comparing temporal changes of the corneal shape from measurement results of the measurement part.

According to second solving means of the invention, there is provided an ophthalmologic apparatus comprising an illuminating optical system for causing a measurement light flux to be incident on a retina of a subject eye, a light receiving optical system for receiving light through a conversion member for dividing a reflected light from the retina of the subject eye into many light fluxes, a light receiving part for converting the received reflected light received by the light receiving optical system into an electrical signal, a wavefront measurement part for obtaining aberration components of the subject eye including higher order aberrations of fifth order or higher from received light signals of the light receiving part obtained plural times at a start point of time after a blink of the subject eye and during a subsequent specified period, and a judgment part for judging a state of a dry eye by comparing temporal changes of the higher order aberrations of fifth order or higher from measurement results of the wavefront measurement part.

BRIEF DESCRIPTION OF THE DRAWINGS

FIG. 18 is a view of Zernike polynomials of (r, t) coordinates.

FIG. 19 is a view of Zernike polynomials of (x, y) coordinates.

DETAILED DESCRIPTION OF THE INVENTION

1. Structure of an Optical System

Figure 1:
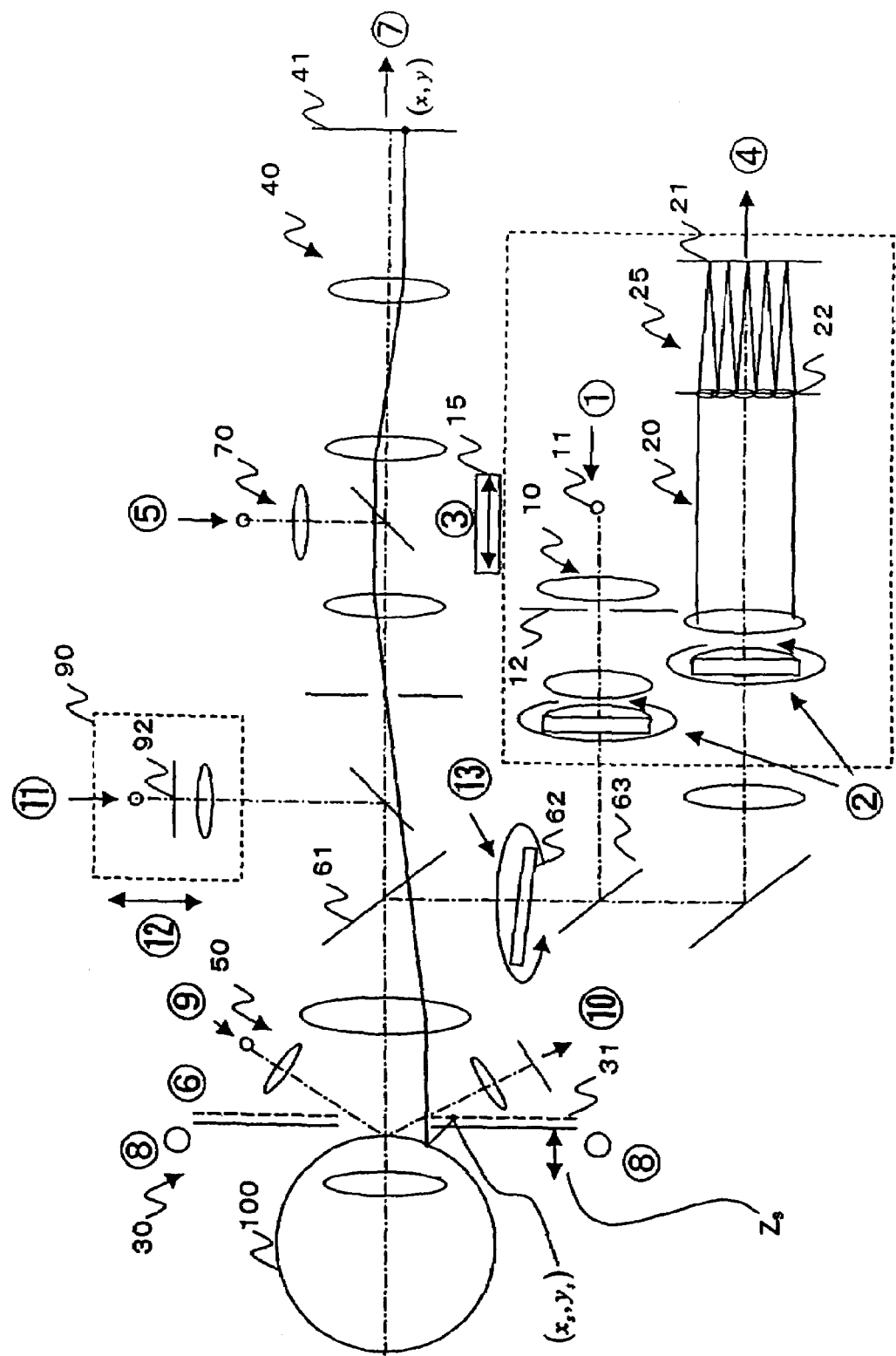
FIG. 1 is a structural view of an optical system of an ophthalmologic apparatus.

FIG. 1 is a structural view of an optical system of an ophthalmologic apparatus.

The ophthalmologic apparatus includes a first illuminating optical system 10, a first light source part 11, a first measurement part 25, an anterior eye part illuminating part 30, an anterior eye part observation part 40, a first adjustment optical part 50, a second adjustment optical part 70, and an index optical part 90. Besides, the first measurement part 25 includes a first light receiving optical system 20 and a first light receiving part 21. Incidentally, with respect to a subject eye 100, a retina (eyeground) and a cornea (anterior eye part) are shown. Besides, the relation among coordinates (x, y), coordinates $(x_s, y_s)$, a distance $Z_s$ and the like will be described later.

Hereinafter, the respective parts will be described in detail.

The first illuminating optical system 10 is for illuminating a minute area on the retina of the subject eye 100 with a light flux from the first light source part 11. The first illuminating optical system 10 includes, for example, a condensing lens, a variable cylinder lens, and a relay lens.

The first light source part 11 emits the light flux with a first wavelength. It is desirable that the first light source part 11 has a high spatial coherence and a not high temporal coherence. Here, as an example, an SOD (Super Luminescence Diode) is adopted for the first light source part 11, and a point light source having high luminescence can be obtained. Incidentally, the first light source part 11 is not limited to the SLD, and a laser having a high spatial coherence and a high temporal coherence can also be used by inserting a rotation diffused plate, a declination prism (D prism) or the like to suitably lower the temporal coherence. Further, an LED having a not high spatial coherence and a not high temporal coherence can also be used, if light quantity is sufficient, by inserting a pinhole or the like at a position of a light source in an optical path. Besides, as a wavelength of the first light source part 11 for illumination, for example, a wavelength (for example, 780 nm) of an infrared range can be used.

The first light receiving optical system 20 is for receiving, for example, the light flux reflected and returned. from the retina of the subject eye 100 and for guiding it to the first light receiving part 21. The first light receiving optical system 20 includes, for example, a first conversion member 22 (for example, a Hartmann plate), an afocal lens, a variable cylinder lens, and a relay lens. The first conversion member 22 is a wavefront conversion member including a lens part for converting the reflected light flux into at least 17 beams when higher order aberrations of fourth order or higher are obtained. As the first conversion member 22, plural micro Fresnel lenses disposed on a plane orthogonal to an optical axis can be used. The first conversion member 22 may include a short focal point and/or high density lens part in addition to a long focal point or high sensitivity one. The reflected light from the retina is condensed on the first light receiving part 21 through the first conversion member 22. The first light receiving part 21 is for receiving the light passing through the first conversion member 22 from the first light receiving optical system 20 and for generating a first signal. Incidentally, the front side focal point of the afocal lens 42 is substantially coincident with the pupil of the subject eye 100.

A movement part 15 moves a portion, as one body, surrounded by a dotted line of FIG. 1 including the first illuminating optical system 10 and the first light receiving optical system 20. For example, it is assumed that the light flux from the first light source part 11 is reflected at a point where it is condensed, they are moved in the direction in which a signal peak at the first light receiving part 21 becomes high, while the relation that the signal peak at the light receiving part 21 due to the reflected light becomes maximum is kept, and they can be stopped at a position where the intensity becomes maximum. Besides, the first illuminating optical system 10 and the first light receiving optical system 20 may be individually moved, and it is assumed that for example, the light flux from the first light source part 11 is reflected at the point where it is condensed, they are moved in the direction where the signal peak at the first light receiving part 21 becomes high, while the relation that the signal peak at the first light receiving part 21 due to the reflected light becomes maximum is kept, and they can be stopped at the position where the intensity becomes maximum.

With respect to the incident light on the subject eye 100 from the first light source part 11, a diaphragm 12 is made eccentric so that an incident position of the light flux is changed to a direction orthogonal to the optical axis, the vertex reflection of the lens and the cornea is prevented, and the noise can be suppressed. The diaphragm 12 has a diameter smaller than the effective range of the Hartmann plate 22, and is designed so that a so-called single path aberration measurement in which the aberration of an eye has an influence on only a light receiving side can be established.

Incidentally, after the incident light beam emitted from the first light source part 11 comes to have a light path common to a measurement light beam diffused and reflected from the retina, it paraxially travels in the same way as the measurement light beam diffused and reflected from the retina. However, in the single path measurement, the diameters of the respective light beams are different from each other, and the beam diameter of the incident light beam is set to be rather small as compared with the measurement light beam. Specifically, the beam diameter of the incident light beam is, for example, about 1 mm at the pupil position of the subject eye 100, and the beam diameter of the measurement light beam can be about 7 mm. Incidentally, by suitably disposing an optical system, a double path measurement can also be performed.

The anterior eye part illuminating part 30 includes a second light source part 31 for emitting a light flux with a second wavelength and illuminates the anterior eye part with the light flux from the second light source part 31 and with a predetermined pattern by using, for example, a Placido disk, a kerato-ring or the like. In the case of the kerato-ring, a pattern of only the vicinity of the center of curvature of the cornea can be obtained by a kerato-image. Incidentally, the second wavelength of the light flux emitted from the second light source part 31 is different from, for example, the first wavelength (here, 780 nm) and a long wavelength can be selected (for example, 940 nm).

The anterior eye part observation part 40 includes a third light receiving part 41 constituted by, for example, a relay lens, a telecentric diaphragm and a CCD, and observes the light flux which is originated from, for example, the pattern of the Placido disk, the kerato-ring or the like by the anterior eye part illuminating part 30 and is reflected and returned from the anterior eye part of the subject eye 100. Incidentally, the telecentric diaphragm is a diaphragm for preventing an anterior eye part image from blurring.

The first adjustment optical part 50 is for mainly performing a working distance adjustment, and includes a light source part, a condensing lens, and a light receiving part. Here, the working distance adjustment is performed in such a manner that for example, a parallel light flux emitted from the light source part and close to the optical axis is irradiated to the subject eye 100, and the light reflected from the subject eye 100 is received by the light receiving part through the condensing lens. Besides, in the case where the subject eye 100 is in a suitable working distance, a spot image from the light source part is formed on the optical axis of the light receiving part. On the other hand, in the case where the subject eye 100 goes out of a suitable working distance, a spot image from the light source part is formed above or below the optical axis of the light receiving part. Incidentally, since the light receiving part has only to detect a change of a light flux position on a plane containing the light source part, the optical axis, and the light receiving part, for example, a one-dimensional CCD disposed on this plane, a position sensing device (PSD) or the like can be applied.

A beam splitter 61 is constructed by, for example, a dichroic mirror which reflects the light flux with the first wavelength and is transparent to the light flux with the second wavelength. Besides, there is disposed a rotary prism 62 for uniforming the light subjected to uneven reflection from the retina. A beam splitter 63 is constructed by a mirror (for example, a polarizing beam splitter) which reflects the light flux from the first light source part 11 and is transparent to the light flux reflected and returned from the retina of the subject eye 100.

The second adjustment optical part 70 is for performing, for example, an alignment adjustment in an XY direction, and includes an optical source part for alignment, a lens, and a beam splitter.

The index optical part 90 includes an optical path for projecting, for example, a scenery chart of the subject eye 100, or an index for fixation or fogging, and includes a light source part (for example, a lamp), a fixed index 92, and a relay lens. The fixed index 92 can be irradiated to the retina by the light flux from the light source part, and the subject eye 100 is made to observe its image.

In the foregoing optical system, although the description has been given to the case where the incident light beam has a thin single path, the invention can also be applied to an ophthalmologic apparatus in which the incident light beam has a thick double path. At that time, although an optical system is disposed by means of a structure for the double path, the measurement and calculation processing by an arithmetic part is the same.

(Conjugate Relation)

The retina of the subject eye 100, the fixed index 92 of the index optical part 90, the first light source part 11, and the first light receiving part 21 are conjugate to each other. Besides, the ocular pupil (iris) of the subject eye 100, the rotary prism 62, the conversion member (Hartmann plate) 22 of the first light receiving optical system, and the diaphragm 12 of the first illuminating optical system 10 at the measurement light incident side are conjugate to each other.

2. Electrical Structure

Figure 2:
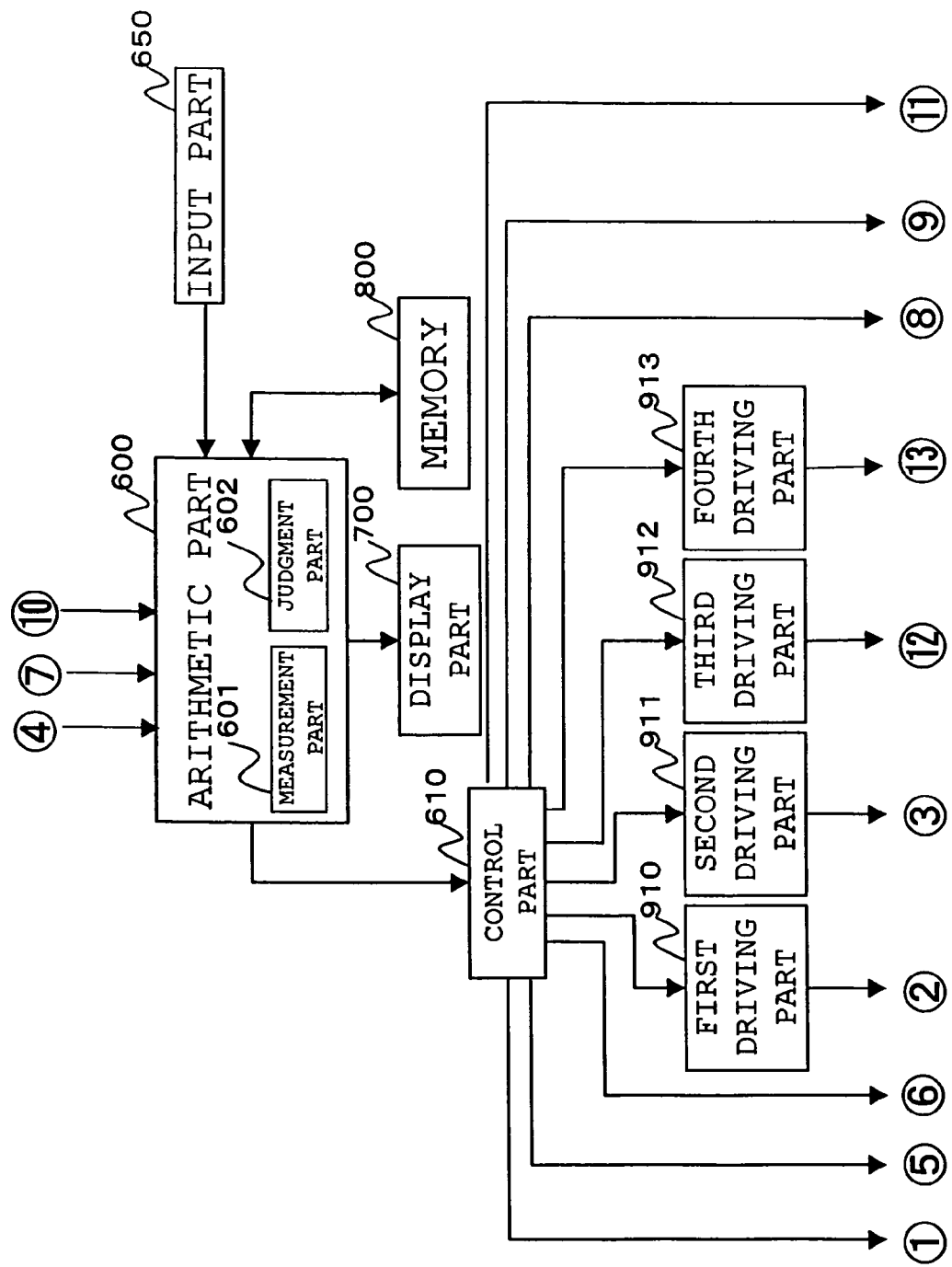
FIG. 2 is a structural view of an electrical system of the ophthalmologic apparatus.

FIG. 2 is a structural view of an electrical system of the ophthalmologic apparatus.

The structure of the electrical system of the ophthalmologic apparatus includes an arithmetic part 600, a control part 610, an input part 650, a display part 700, a memory 800, a first driving part 910, a second driving part 911, a third driving part 912, and a fourth driving part 913. The input part 650 includes a pointing device for indicating suitable buttons, icons, positions, areas and the like displayed on the display part 700, a keyboard for inputting various data, and the like.

The arithmetic part 600 includes a measurement part 601 and a judgment part 602.

According to an embodiment, the measurement part 601 obtains the corneal shape of the subject eye from the light receiving signal of the first light receiving part plural times at a measurement start point of time and during a subsequent specified period. The judgment part 602 judges the state of the dry eye by comparing temporal changes of the corneal shape from the measurement results of the measurement part 601.

Besides, according to another embodiment, the measurement part 601 can be constructed to measure wavefront aberrations of the subject eye on the basis of the divided light fluxes by the first conversion member 22 from the received light signals of the first light receiving part 21 during a specified period from a start point of time after the subject eye blinks. In this case, the measurement part 602 can be constructed to judge the state of the dry eye by comparing the measurement result based on the corneal shape obtained by the measurement part 601 and the temporal change of the measurement result based on the wavefront aberrations.

Further, according to still another embodiment, the measurement part (wavefront measurement part) 601 performs a measurement of wavefront aberrations plural times during a specified period. The judgment part 602 judges the state of the dry eye by comparing the temporal changes of the plural measurement results of the wavefront aberrations.

The arithmetic part 600 receives a first signal (4) from the first light receiving part 21, a signal (7) from the anterior eye part observation part 40, and a signal (10) from the first adjustment optical part 50. The arithmetic part 600 receives the first signal (4) from the first light receiving part 21 and the signal (7) from the anterior eye part observation part 40, and obtains the optical characteristic of the subject eye 100 on the basis of, for example, inclination angles of the light fluxes. The arithmetic part 600 suitably outputs signals corresponding to the arithmetical operation results of these or other signals and data to the control part 610 for performing the control of the electrical drive system, and to the display part 700 and the memory 800.

The control part 610 is for controlling the lighting and extinction of the first light source part 11 and the second light source part 31, and for controlling the first driving part 910 to the fourth driving part 913 on the basis of the control signals from the arithmetic part 600. For example, on the basis of the signals corresponding to the arithmetical operation results in the arithmetic part 600, the control part 610 outputs a signal (1) to the first light source part 11, outputs a signal (5) to the second adjustment optical part 70, outputs a signal (6) to the anterior eye part illuminating part 30, outputs signals (8) and (9) to the first adjustment optical part 50, outputs a signal (11) to the index optical part 90, and further outputs signals to the first driving part 910 to the fourth driving part 913.

The first driving part 910 outputs a signal (2) on the basis of the signal (4) inputted to the arithmetic part 600 from the first light receiving part 21, and drives suitable lens movement means to rotate the variable cylinder lens of the first illuminating optical system 10 and the variable cylinder lens of the first light receiving optical system 20. The variable cylinder lens may not be provided.

The second driving part 911 is for moving the first illuminating optical system 10 and the first light receiving optical system 20 in the optical axis direction on the basis of the received light signal (4) inputted to the arithmetic part 600 from the first light receiving part 21, and outputs a signal (3) to the movement part 15, and drives the lens movement means of the movement part 15. The first light receiving optical system 20 is moved in the optical axis direction, so that the compensation of low order aberrations can be performed.

The third driving part 912 is for moving, for example, the index optical part 90, and outputs a signal (12) to a not-shown suitable movement means and drives this movement means. The fourth driving part 913 is for rotating the rotary prism 62, and outputs a signal (13) to a not-shown suitable leans movement means and drives this lens movement means.

3. Measurement Flowchart

3-1. Measurement Flowchart of a Dry Eye (First Embodiment)

Figure 3:
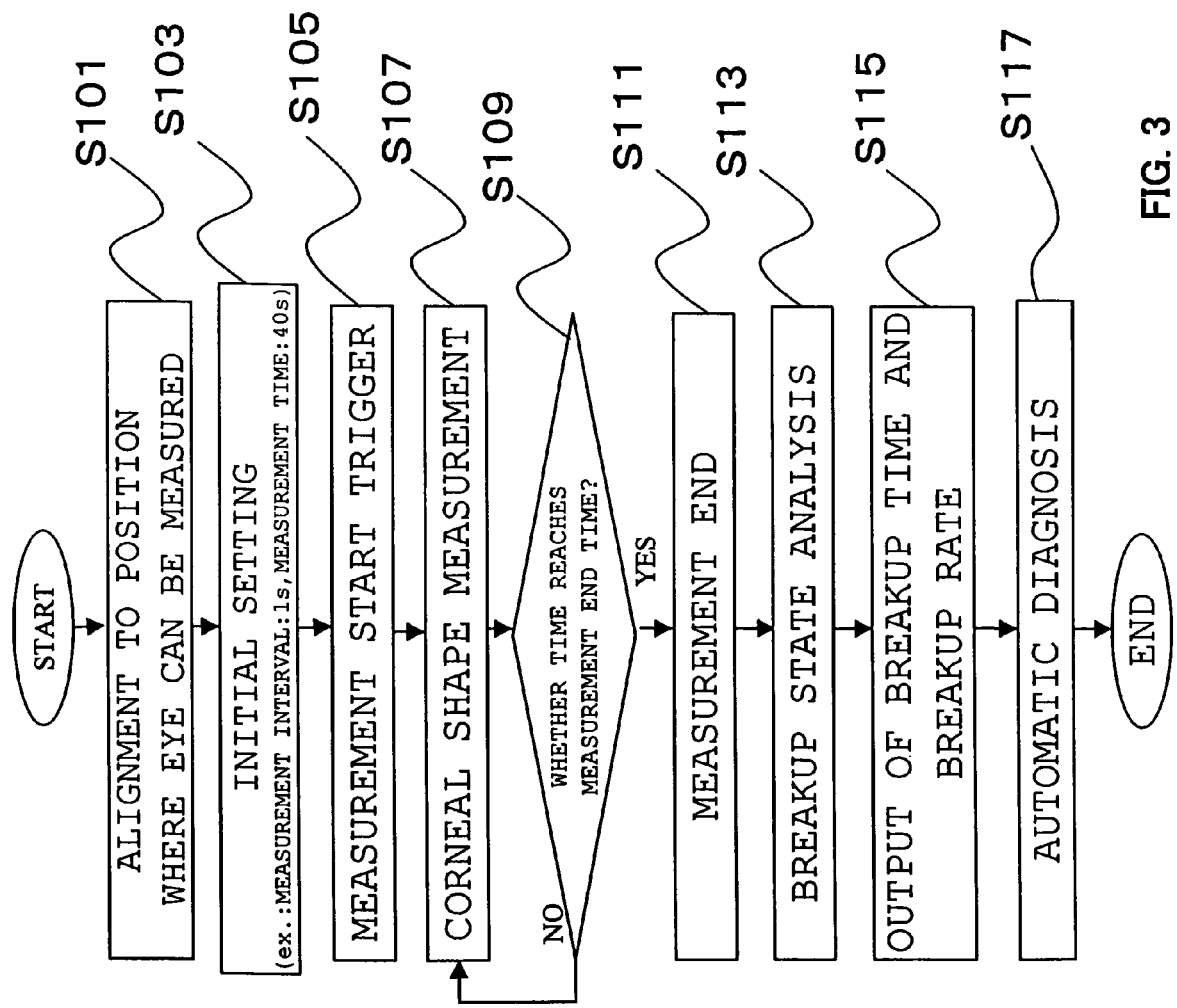
FIG. 3 is a measurement flowchart of a dry eye according to a first embodiment.

FIG. 3 shows a measurement flowchart of a dry eye according to a first embodiment.

When a test subject comes to a measurement position and a measurement is started, the ophthalmologic apparatus is aligned at a position where an eye can be measured (S101). This alignment may be performed manually or automatically. For the measurement of the corneal shape, it is necessary to fix the positions of the cornea and the ophthalmologic apparatus within a specified range. The ophthalmologic apparatus is manually or automatically controlled so as to fix the front and back, right and left, and up and down positions. For example, on the basis of any one of or more than one of the Placido disk (kerato-ring), a light point from infinity, a point of parallel projection, and a contour of the cornea, an operator can manually keep the alignment, or the alignment can be automatically kept by an auto alignment function of the apparatus itself.

Next, the arithmetic part 600 makes an initial setting of the apparatus by the measurement part 601 (S103). The measurement part 601 sets, for example, a measurement interval to be one second, and a measurement time to be 40 seconds. The input part 650 or the arithmetic part 600 acts as a trigger for the measurement start (S105). The trigger can be previously set such that for example, the operator operates the measurement start button, or the blink after the operation of the measurement start button is measured and the measurement is started at that timing. In accordance with the trigger, the measurement part 601 carries out a corneal shape measurement processing for measuring the corneal shape and corneal wavefront aberrations (S107). The details of the corneal shape measurement processing will be described later. Here, the arithmetic part 600 repeats the corneal shape measurement processing by the measurement part 601 until time reaches the measurement end time, and obtains the corneal shape and the corneal wavefront aberrations (S109). In case a blink occurs before the time reaches the measurement end time, the measurement is ended at the point of time. The arithmetic part 600 ends the measurement when the time reaches the measurement end time (S111).

Next, the judgment part 602 of the arithmetic part 600 analyzes a breakup state as one index for judgment of the state of the dry eye (S113). The details will be described later. The judgment part 602 obtains values of a breakup time (start time), a breakup speed, a breakup amount, a breakup rate and the like on the basis of the breakup state, outputs them to the display part 700, and stores them in the memory 800 (S115) Next, the judgment part 602 performs an automatic diagnosis relating to the dry eye on the basis of the respective obtained values relating to the breakup, outputs it to the display part 700, and stores it in the memory 800 (S117). With respect to the automatic diagnosis of the dry eye, for example, in accordance with specified settings, a judgment is made as to whether (1) the breakup start point is early, (2) the breakup rate is high, or (3) both the conditions are satisfied, and when the respective conditions (1) to (3) exceed a certain boundary, it can be judged that the eye is the dry eye. In this way, the processing is ended. Incidentally, care can be given such that during this measurement, a stimulus to the eye is suppressed by instillation anesthesia or the like to inhibit the blink.

3-2. Analysis of a Breakup State

Figure 4:
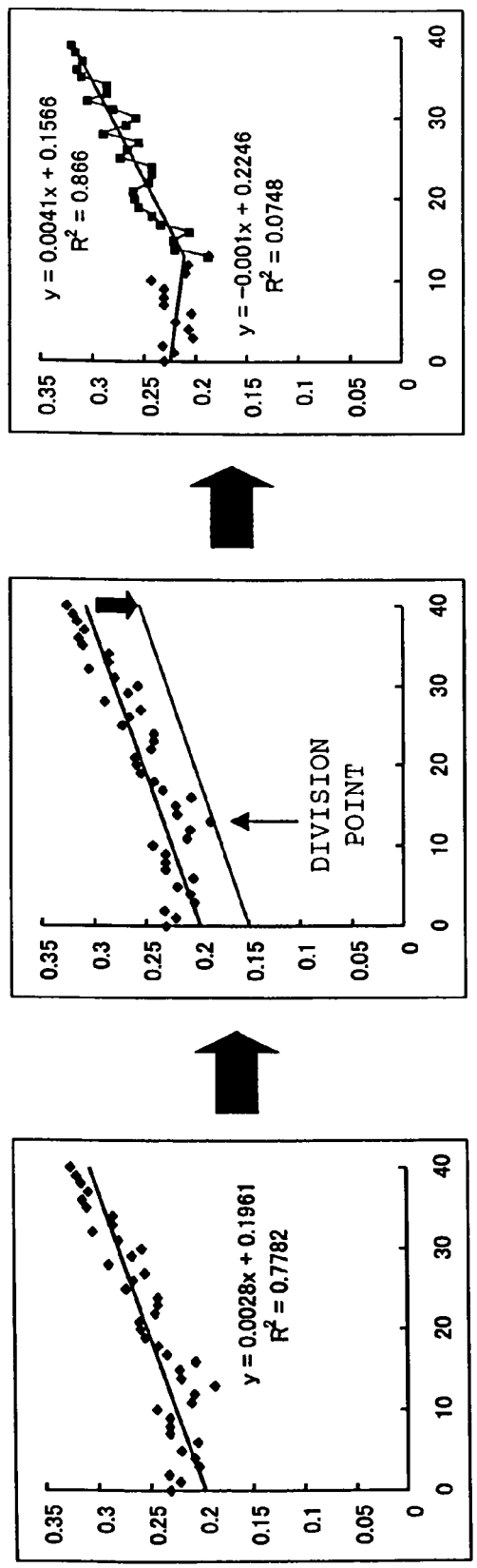
FIG. 4 is an explanatory view for obtaining a breakup (division point).

FIG. 4 is an explanatory view for obtaining a breakup (division point).

In this drawing, the horizontal axis indicates the number of measurement times and the vertical axis indicates the RMS of higher order aberrations. In the drawing, the division point is made the start point of the breakup of the tear film. The left side of the division point is made a steady state of the tear film, and the inclination of a regression line at this time is made a steady state (inclination is ideally 0). On the other hand, the right side of the division point is made the breakup state. Incidentally, for example, the inclination of a regression line in this area can be made the breakup rate.

Figure 5:
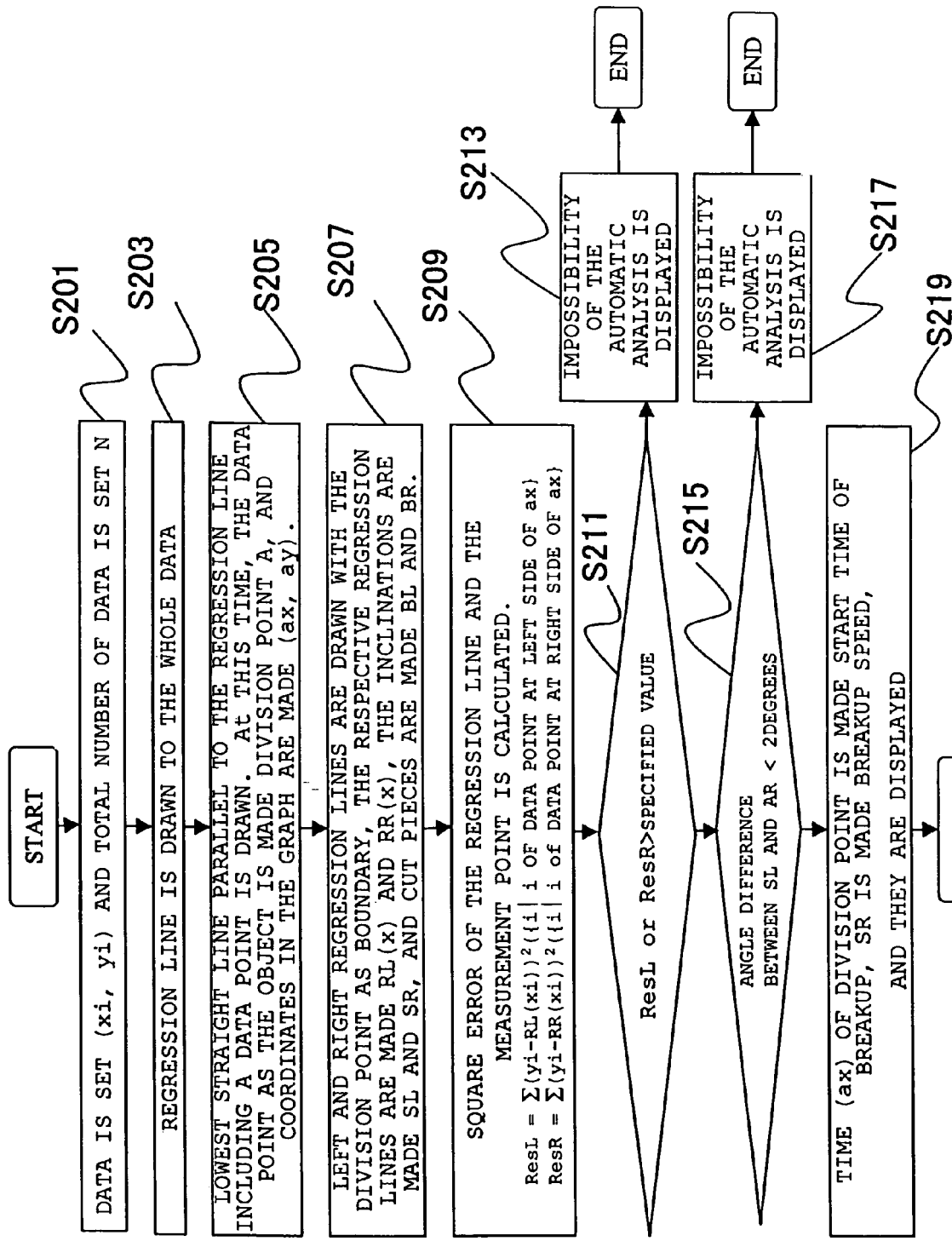
FIG. 5 is an analysis flowchart for obtaining the breakup.

FIG. 5 shows an analysis flowchart for obtaining the breakup. Here, the judgment part 602 of the arithmetic part 600 approximates measurement data to two straight lines, so that the breakup can be obtained as shown in FIG. 4.

When the processing is started, the judgment part 602 sets, for example, the data to be $x_i$ and $y_i$, and sets the total number of data to be N (S201). The judgment part 602 draws a regression line to the whole data (S203). For example, the judgment part 602 draws the lowest straight line (or a line separated from the lowest by a predetermined number) parallel to the regression line containing the data point. Here, the judgment part 602 sets the objective data point at this time to be a division point A, and sets the coordinates in the graph to be (ax, ay) (S205). Besides, the judgment part 602 draws left and right regression lines with the division point as the boundary, and the respective regression lines are made RL (x) and RR (x), inclinations thereof are made SL and SR, and cut pieces are made BL and BR (S207). The judgment part 602 calculates square errors of the regression lines and the measurement points (S209). The judgment part 602 can calculate the square errors ResL and ResR with respect to the left and right regression lines as indicated by, for example, following expressions.

$$ResL = \Sigma(yi - RL(xi))^2 (\{i|i \text{ of data point at left side of } ax\})$$

$$ResR = \Sigma(yi - RR(xi))^2 (\{i|i \text{ of data point at right side of } ax\})$$

In the case where the calculated ResL and/or ResR exceeds a preset specified value (S211), the judgment part 602 displays that the automatic analysis is impossible on the display part 700 (S213), and ends the processing. On the other hand, When ResL and/or ResR is not larger than the specified value (S211), and in the case where an angle difference between SL and SR is a predetermined value (for example, 2 degrees) or less (S215), the judgment part 602 displays that the automatic analysis is impossible on the display part 700 (S217), and ends the processing. On the other hand, in the case where the angle difference between SL and SR exceeds the predetermined value (S215), the judgment part 602 sets the time of the division point to be the start time of the breakup, sets SR to be the breakup speed, obtains respective values. relating to the breakup, displays them on the display part 700, and stores them in the memory 800 (S219). Further, the structure may be such that the operator finally makes confirmation on the display part 700, and can move the division point by the input part 650.

Figure 6:
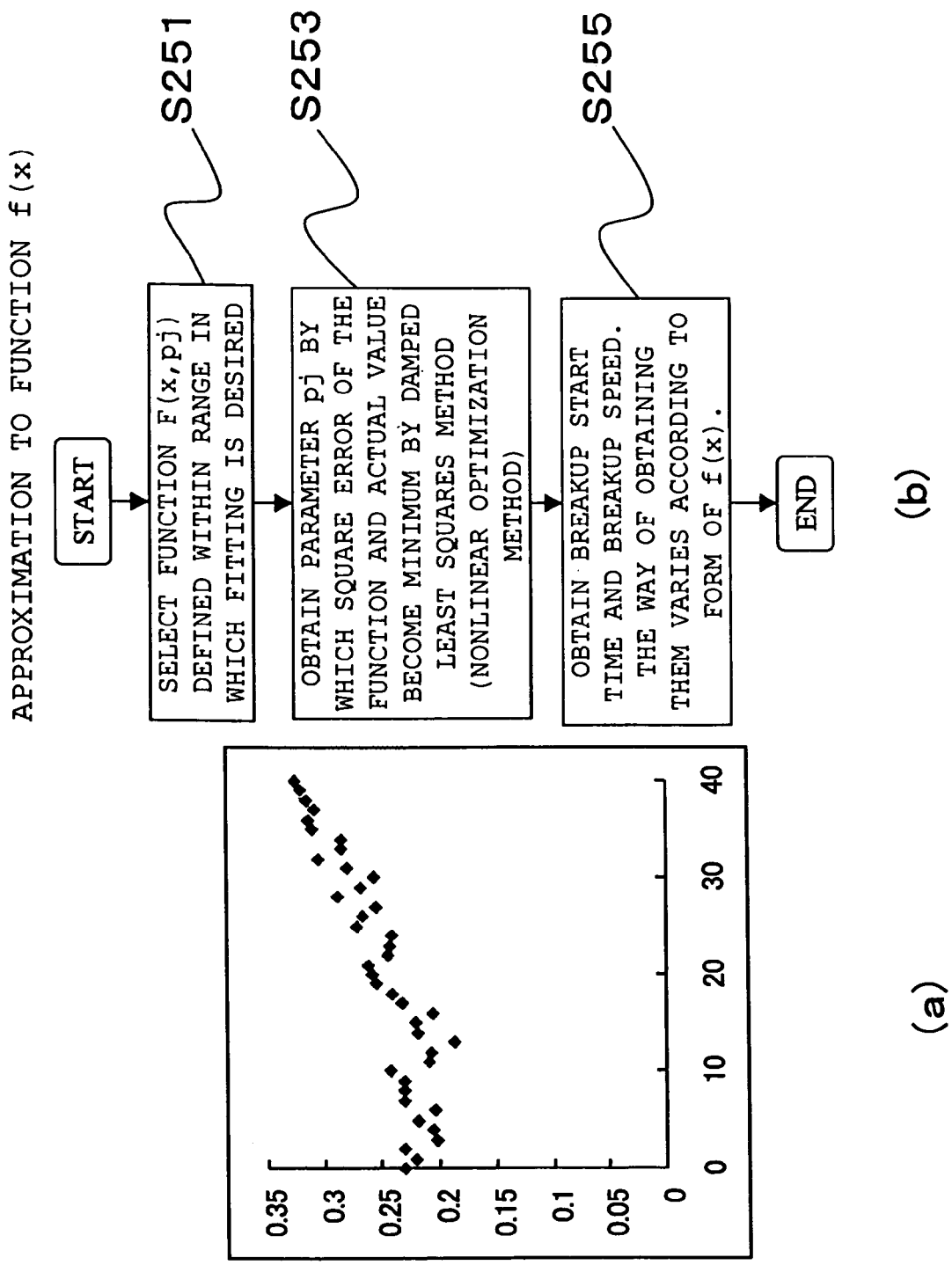
FIG. 6 is another analysis flowchart for obtaining the breakup.

Next, FIG. 6 shows another analysis flowchart for obtaining the breakup. Here, the judgment part 602 approximates measurement data to a function f(x).

When the processing is started, the judgment part 602 selects a function F(x, pj) defined in a range in which a fit is desired to be made (S251). Incidentally, x indicates the horizontal axis of the graph, and pj indicates a parameter (it may be two or more parameters) obtained by optimization. Next, the judgment part 602 obtains such a parameter pj by a generally known damped least squares method (nonlinear optimization method) that the square error of the function and the actual measurement value becomes minimum (S253). Next, in accordance with the function f(x) determined by the obtained parameters, the judgment part 602 obtains values relating to the breakup, such as the breakup start time and the breakup speed (S255). Incidentally, these values can be suitably obtained in the form of f(x) In this way, the processing is ended.

Incidentally, as an example of the function form, there is a polygonal line as indicated-by a following expression.

$$f(x) \Leftrightarrow \begin{cases} f_1(x) = k_1(x-a)+b & \text{for } x < a, \\ f_2(x) = k_2(x-a)+b & \text{for } x > a. \end{cases}$$

Here, parameters to be determined by the optimization are $k_1$, $k_2$, a and b. Incidentally, the initial values of those may be arbitrary, or may be determined by the method used in the foregoing algorism. In this function form, the breakup start time is a, and an optimized value of $k_2$ is adopted as the breakup speed.

Besides, there is also a method in which in the case where the output can not be obtained by the foregoing algorism, the parameters $k_1$, $k_2$, a and b are obtained by its final fitting, they are used as the initial values of the algorism, and the result of the above expression is outputted.

3-3. Measurement of Corneal Shape (S107)

Figure 7:
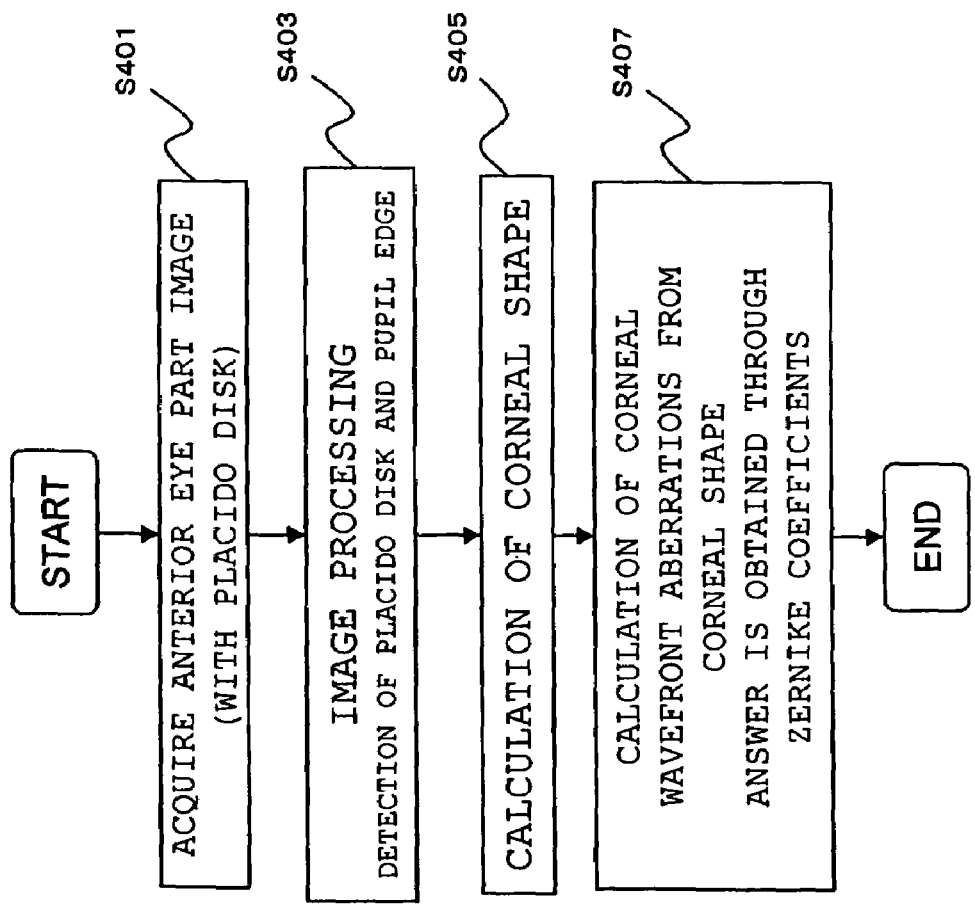
FIG. 7 is a flowchart of corneal shape measurement.

FIG. 7 is a flowchart of a corneal shape measurement. This corresponds to the step S107 of FIG. 3.

First, the measurement part 601 acquires an anterior eye part image (with a Placido disk) (S401). The acquired image is suitably stored in the memory 800 or the like. The measurement part 601 carries out an image processing of the anterior eye part image, and detects the Placido disk and the pupil edge (S403). The measurement part 601 calculates the corneal shape on the basis of the detected data (S405). The measurement part 601 calculates corneal wavefront aberrations from the calculated corneal shape (S407). Here, the calculation result is obtained as Zernike coefficients.

Hereinafter, the details of the respective steps will be described.

(Anterior Eye Part Image: S401)

At step S401, the following anterior eye part image is acquired.

Figure 8B:
FIGS. 8A and 8B are explanatory views of the temporal change of a corneal shape.
Figure 8A:
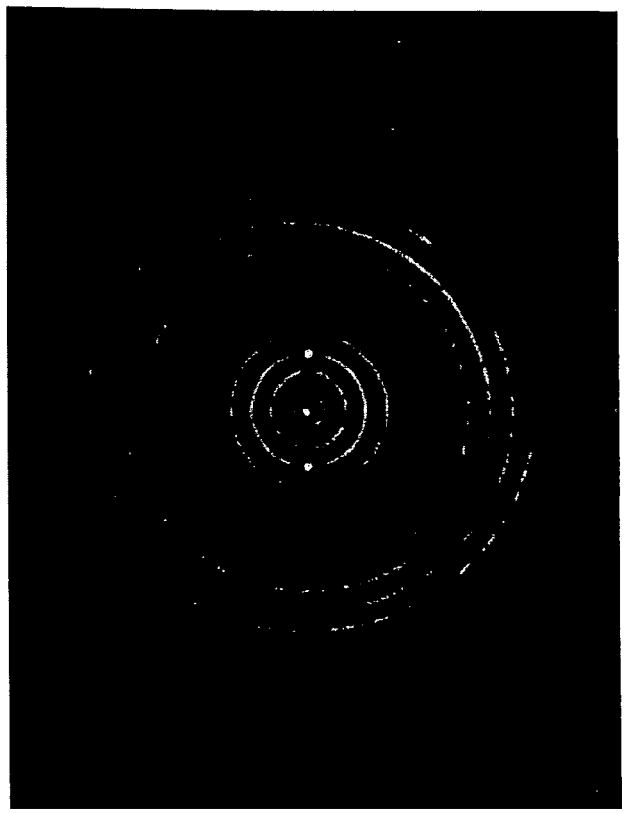

FIGS. 8A and 8B are explanatory views of the temporal change of the corneal shape.

FIG. 8A shows a state immediately after the measurement start, and when analyzed, the corneal wavefront aberrations are relatively small. On the other hand, FIG. 8B shows a state where 30 seconds has passed since the measurement started, and the image of the Placido disk blurs, and when analyzed, the corneal wavefront aberrations are relatively large.

Figure 9B:
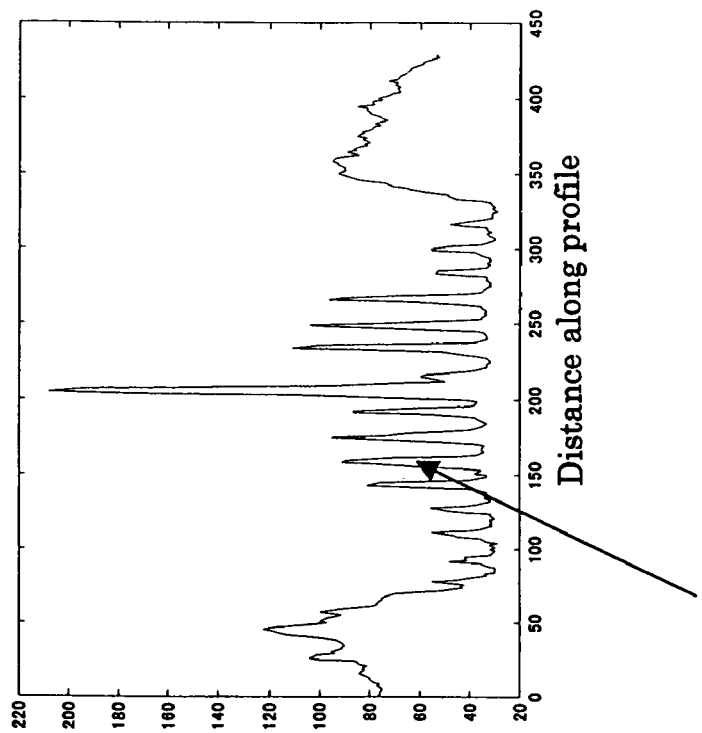
FIGS. 9A and 9B are explanatory views of the temporal change of a blur of a Placido' disk image.
Figure 9A:
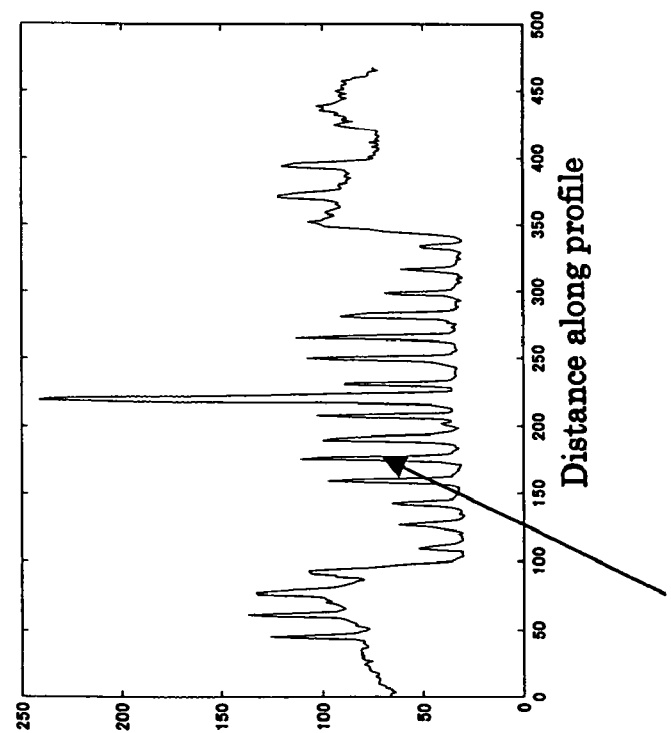

Incidentally, FIGS. 9A and 9B are explanatory views of the temporal change of the blur of the Placido disk image.

FIG. 9A shows the state immediately after the measurement start, and as indicated by an arrow, a reflected image is clear, and the width of the reflected image of the Placido disk is narrow. On the other hand, FIG. 9B shows the state where a predetermined time has passed since the measurement started, and as indicated by an arrow, the reflected image blurs, and the width of the reflected image of the Placido disk is wide.

(Image Processing: S403)

Figure 10:
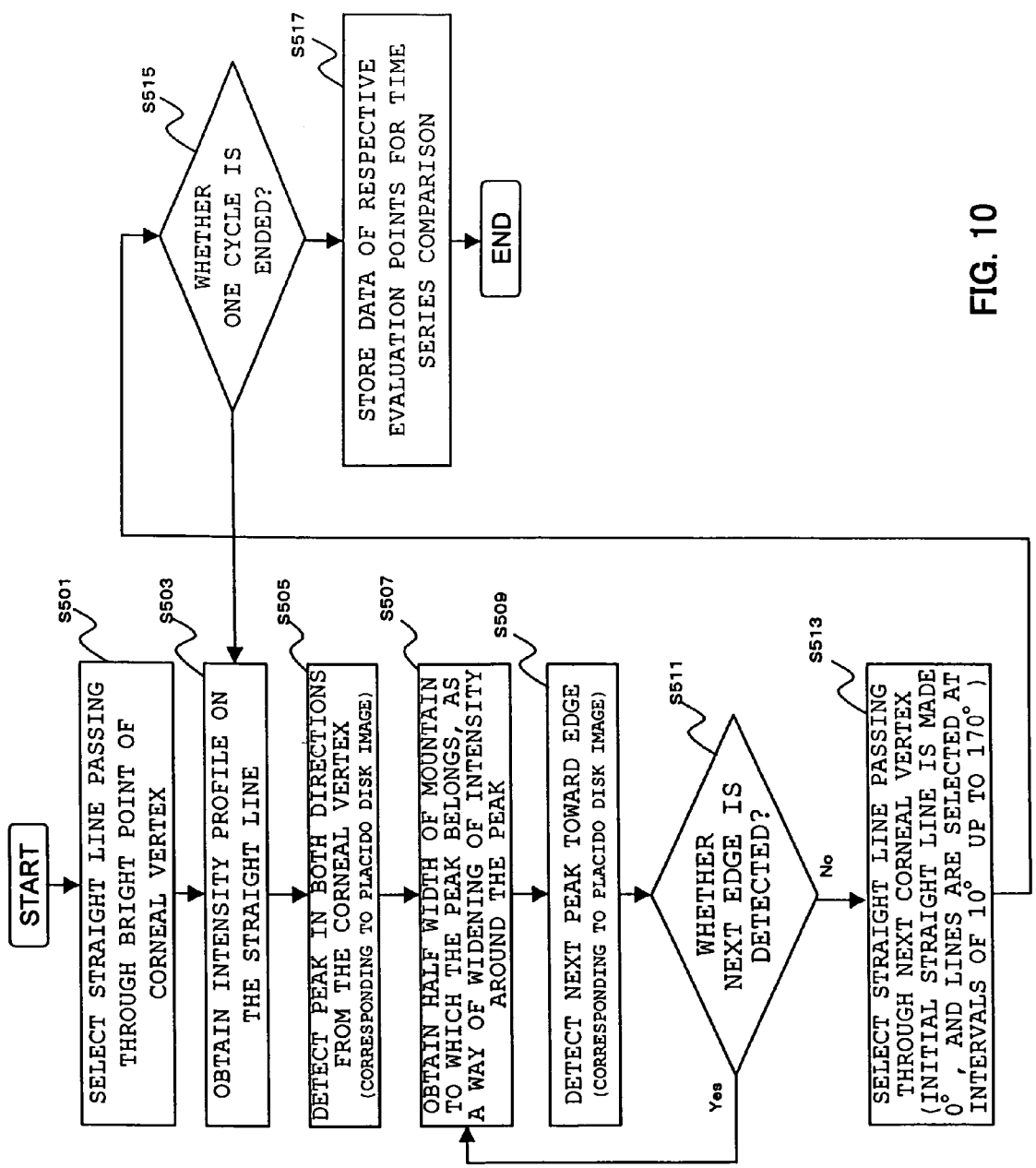
FIG. 10 is a flowchart of an image processing of detection of a Placido's disk and a pupil edge.

FIG. 10 shows a flowchart of an image processing of detection of the Placido disk and the pupil edge. This corresponds to the step S403.

Figure 11:
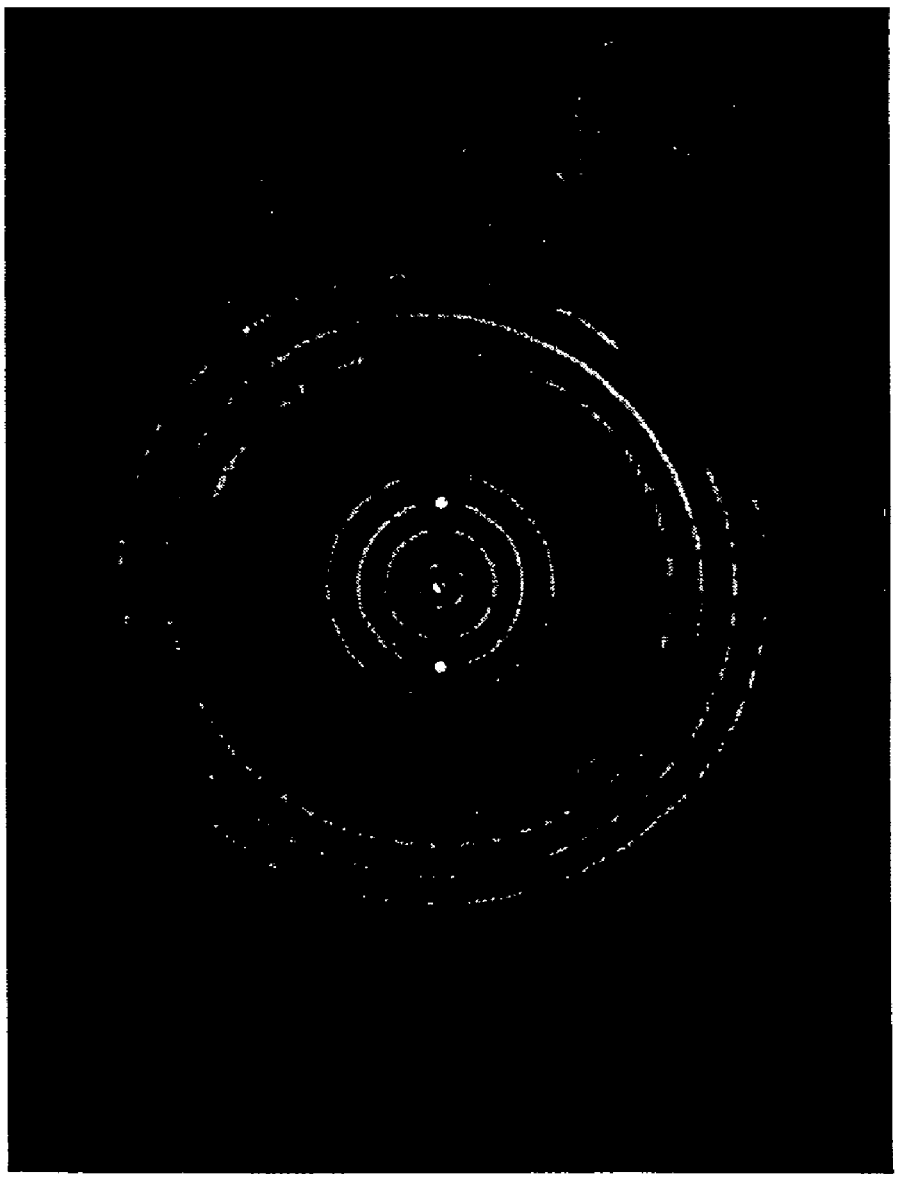
FIG. 11 is an explanatory view of the image processing.

Besides, FIG. 11 is an explanatory view of the image processing.

First, as shown in FIG. 11, the measurement part 601 selects a straight line passing through a bright point of the vertex of the cornea on the basis of the acquired anterior eye part image (S501). Next, as shown in FIGS. 9A and 9B, the measurement part 601 obtains an intensity profile on the straight line (S503). On the basis of the profile, the measurement part 601 detects peaks in both directions from the vertex of the cornea (S505) (corresponding to the Placido disk image). Besides, as a way of widening of intensity around the peak, the measurement part 601 obtains the half width of a mountain to which the peak belongs (S507). Further, the measurement part 601 detects a next peak toward the edge (S509) (corresponding to the Placido disk image). The measurement part 601 judges whether the next edge can be detected (S511), and repeats the steps S507 and S509 until it becomes impossible to detect the edge.

Next, the measurement part 601 selects a straight line passing through a next vertex of the cornea (S513) (for example, the first straight line is made 0 degree, and lines are selected at intervals of 10 degrees up to 170 degrees). The measurement part 601 judges whether one cycle is ended (S515), and repeats the processing subsequent to the step S503 until one cycle is ended. Thereafter, the measurement part 601 stores the data of the respective evaluation points into the memory 800 for time series comparison (S517). In the data of the corneal shape obtained in this way, for example, the peak value or the coordinate value (ring position) of the barycenter and the intensity and/or the half width are stored in a time series for every ring and angle.

(Calculation Method of Corneal Shape: S405)

Hereinafter, the step S405 will be described. As an example, a measurement method of the corneal shape will be described along "Rand RH, Howland HC, Applegate RA "Mathematical model of a placido disk karatometer and its implications for recovery of corneal topography", Optometry and Vision Science 74 (1997) p 926–930".

It is assumed that the corneal shape is expressed by a following function.

$$Z_c = f(x, y).$$

Where, x and y indicate coordinates on the cornea.

As shown in FIG. 1, a light beam from a certain Placido disk forms an image at a point on the image pickup device. The position of the Placido disk is made $(x_s, y_s)$, and a point on the cornea conjugate to a corresponding point on the image pickup device of the third light receiving part 41 is made (x, y). A distance from the Placido disk to the reference surface (zero position) of the function of the cornea is made $Z_s$. The relation of these is expressed by a following pair of expressions.

$$x_s = \frac{2(z_s - f)}{f_x^2 + f_y^2 - 1} f_x, \quad y_s = \frac{2(z_s - f)}{f_x^2 + f_y^2 - 1} f_y$$

Where, with respect to $Z_s$, the working distance adjustment part 50 in the drawing can control it or know the accurate distance value. Incidentally, fx denotes a partial differentiation of the function f with respect to x, and $f_y$ denotes a partial differentiation with respect to y.

Here, since the circular Placido disk is adopted, it is rotation symmetric with respect to the axis in the drawing, and is expressed by $$\sqrt{(x_s^2 + y_x^2)} = \text{Constant}$$

and it is assumed that the Constant (constant value) is expressed by $r_s$ (note that this is a value of the apparatus and is already known). Then, since it is known, at the stage of the image processing by the arithmetic part 600, that the position of the point to be measured on the image pickup device belongs to which ring, when the relation of (group of coordinates of points on the image pickup device) versus (radius of ring) is digitized at, for example, 360 points on each ring of eleven rings, the data pairs of the relation corresponding to this can be formed.

Here, the expansion of Zernike polynomials is adopted as the function. Since the normal cornea can be regarded as having no higher order shape change, when an analysis diameter is about 6 mm, the expansion is stopped at approximately the sixth order, and it can be expressed by $$f(x, y) = \sum_{j=i, -i+2 \ldots i-2, i}^{6} c_i^j Z_i^j(x/r_n, y/r_n)$$

Where, $r_n$ indicates a radius to be analyzed, and is used for normalization.

This Zernike expansion is inserted in the two preceding relational expressions, and when it is used that the Placido disk is rotation symmetric, the coefficient $c_i^j$ can be determined by using a nonlinear least square method. When the coefficient determined by this is again inserted in the Zernike expansion, the function f(x, y) is determined, and the corneal shape is obtained.

(Calculation Method of Corneal Wavefront: S407)

Hereinafter, the step S407 will be described. Since the corneal shape is obtained, it is well known that the strict corneal wavefront aberrations in the geometry can be obtained from the ray tracing of an aspheric surface known in optical design. Here, as an example, a method of obtaining a corneal wavefront aberrations very simply will be described.

For example, with respect to the corneal wavefront aberrations with a diameter of 6 mm on the cornea, the corneal shape is approximated by a sphere with appropriate radius (called a reference spherical surface), a difference between the actual corneal shape and the reference spherical surface is obtained, and this is multiplied by the refractive indexes (n−1) of air and the cornea, so that the corneal wavefront aberrations can be obtained from the corneal shape. However, since the spherical aberrations occur from the original reference spherical surface as well, this is added. By this, the corneal wavefront aberrations can be obtained within an approximation accuracy of 5%.

3-4. Ophthalmologic Measurement for Analyzing a Dry Eye While a Blink is Made a Trigger Next, a description will be given to an ophthalmologic measurement for analyzing a dry eye while a blink is made a trigger.

Steps S101 and S103 are as described above. At step S105, the test subject is instructed to naturally blink in an easy state, and the measurement start button of the input part 650 is pressed. Next, at step S107 and S109, the arithmetic part 600 starts a Hartmann continuous measurement (intervals of one second) by the measurement part 601. Further, here, the measurement part 601 starts an anterior eye part continuous measurement (intervals of one second), obtains the histogram relating to the brightness every time, and judges the blink from this.

Figure 12:
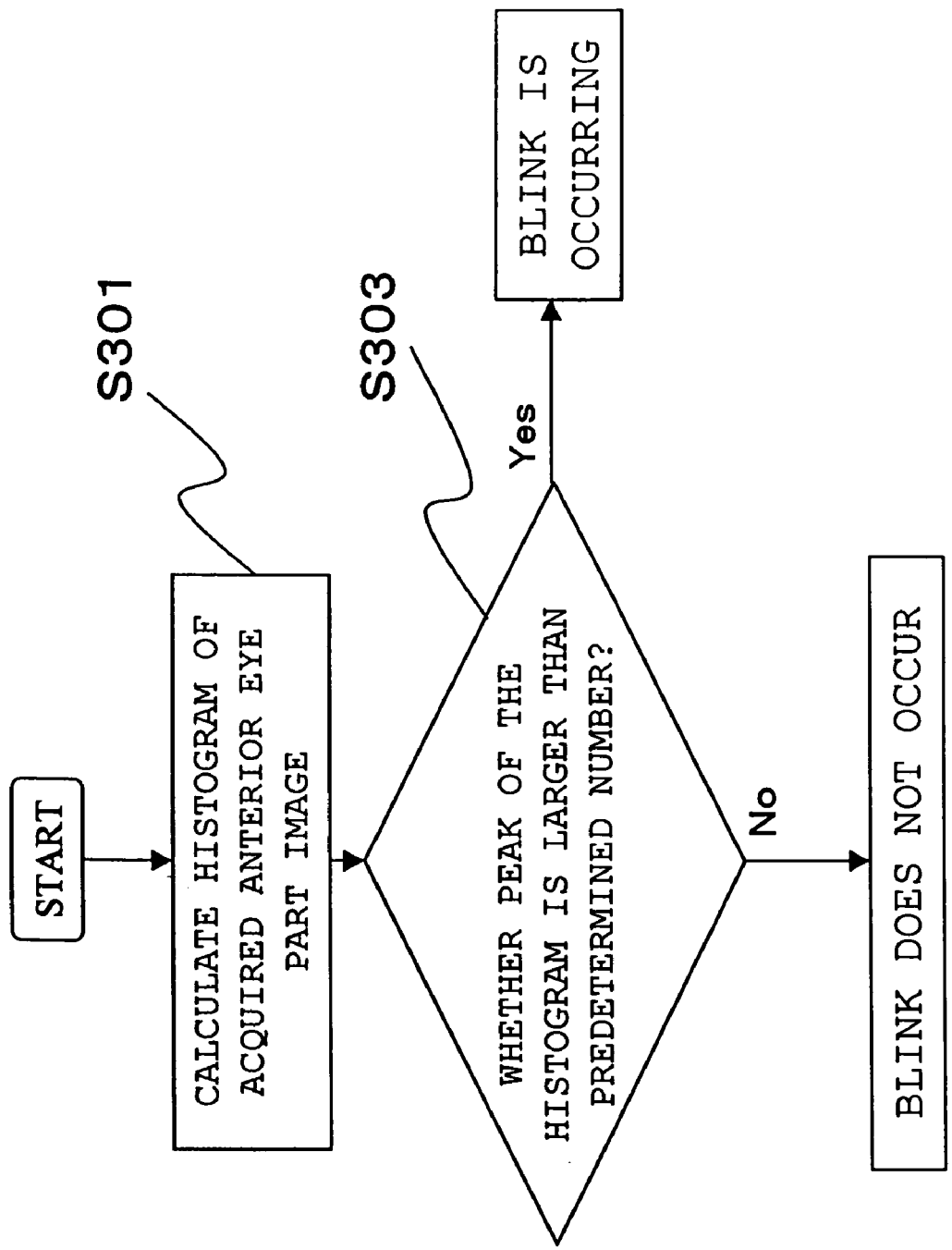
FIG. 12 is a judgment flowchart of a blink.
Figure 13A:
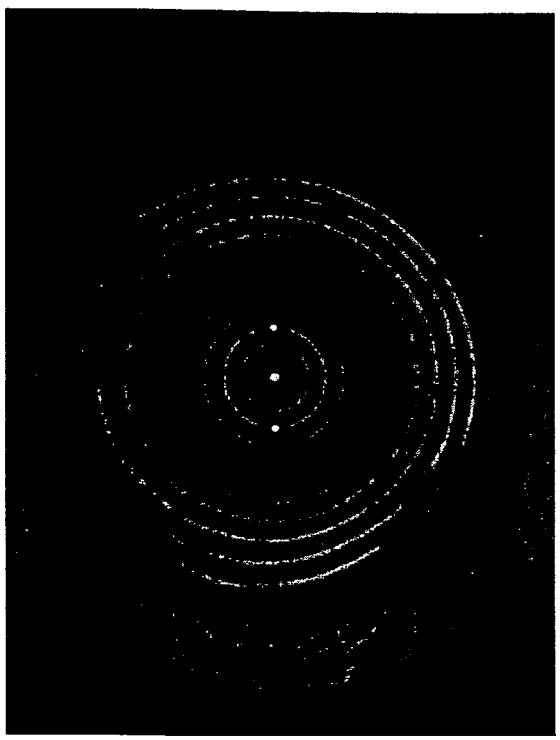
FIGS. 13A and 13B are explanatory views concerning a histogram at the time when a blink does not occur.
Figure 13B:
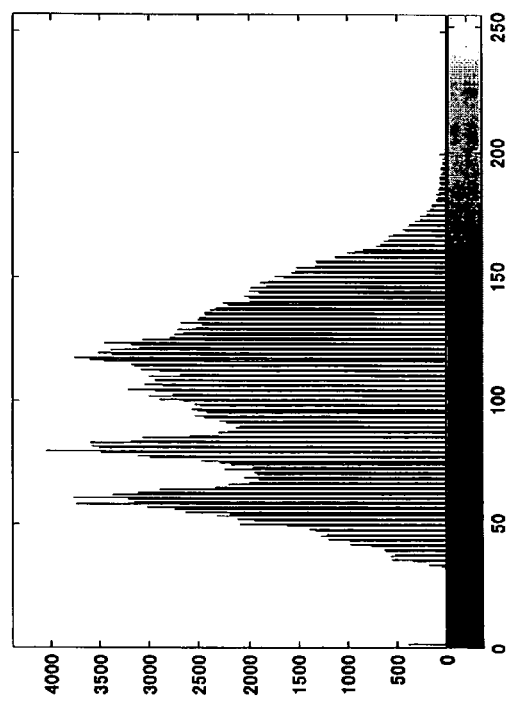
Figure 14A:
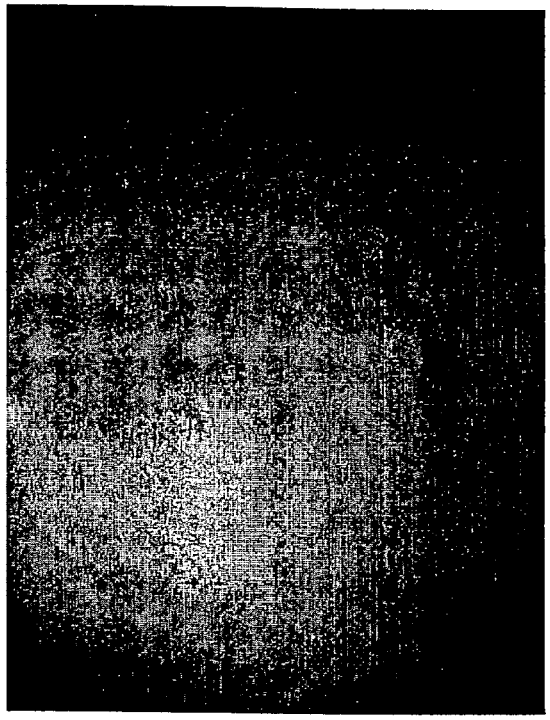
FIGS. 14A and 14B are explanatory views concerning a histogram during the blink.
Figure 14B:
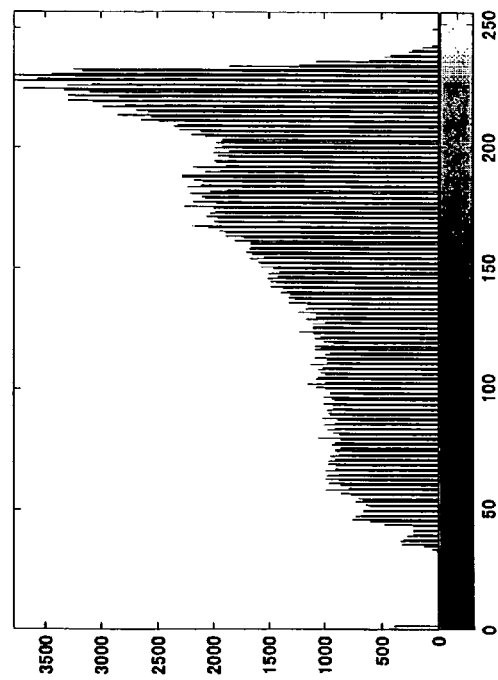

FIG. 12 is a judgment flowchart of the blink. Besides, FIGS. 13A and 13B and FIGS. 14A and 14B are respectively explanatory views of histograms at the time when a blink does not occur and at the time when a blink is occurring. FIGS. 13A and 14A show anterior eye part images, and FIGS. 13B and 14B show histograms.

When the judgment flowchart of the blink is started, the judgment part 602 of the arithmetic part 600 calculates the histogram of the acquired anterior eye part image (S301). The judgment part 602 compares the peak of the histogram with a predetermined number (for example, 150). Here, in the case where the peak is larger than the predetermined number, it is judged that the blink is occurring (see FIGS. 14A and 14B), and on the other hand, in the case where the peak is smaller, it can be judged that the blink does not occur (see FIG. 13).

Next, returning to the main flow, for example, the test subject is instructed to suppress the blink after one blink occurs. When the end time of the final blink is made to, the judgment part 602 ends the measurements of the Hartmann and the anterior eye part when a predetermined time has passed since to.

Thereafter, at the processing subsequent to the step S113, the judgment part 602 of the arithmetic part 600 uses the image after to to perform the analysis by the foregoing algorism similarly to the above, and obtains respective values relating to the breakup, such as a breakup start time and speed.

Figure 21:
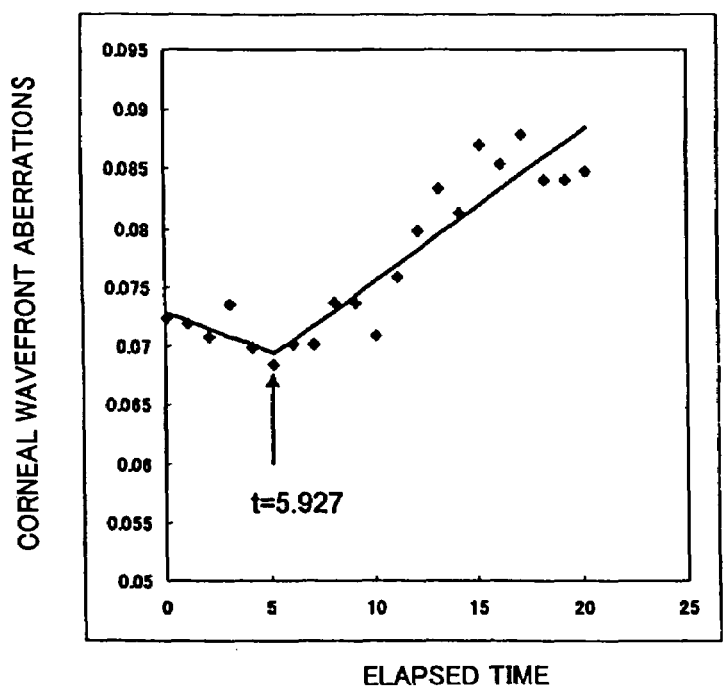
FIG. 21 is a view of a measurement example. (1) of the breakup.

FIG. 21 shows a measurement example (1) of the breakup.

This drawing shows the measurement example of the breakup through the corneal wavefront aberrations obtained from the corneal shape, and shows the result in which the state of the breakup for a certain test subject is measured by the ophthalmologic apparatus of this embodiment. As shown in the drawing, the respective values of the breakup start time and the like are obtained by a regression line.

Incidentally, as the alignment during the measurement, since the measurement is carried out for, for example, about 20 seconds, an auto alignment is preferable as the alignment. Besides, a mechanism may be provided in which an operator makes an alignment manually. Further, the degree of eye fatigue can also be measured by obtaining the number of times of blinking, or by performing a measurement as to whether a dry portion still exists though a tear film is recovered by a blink.

Figure 15:
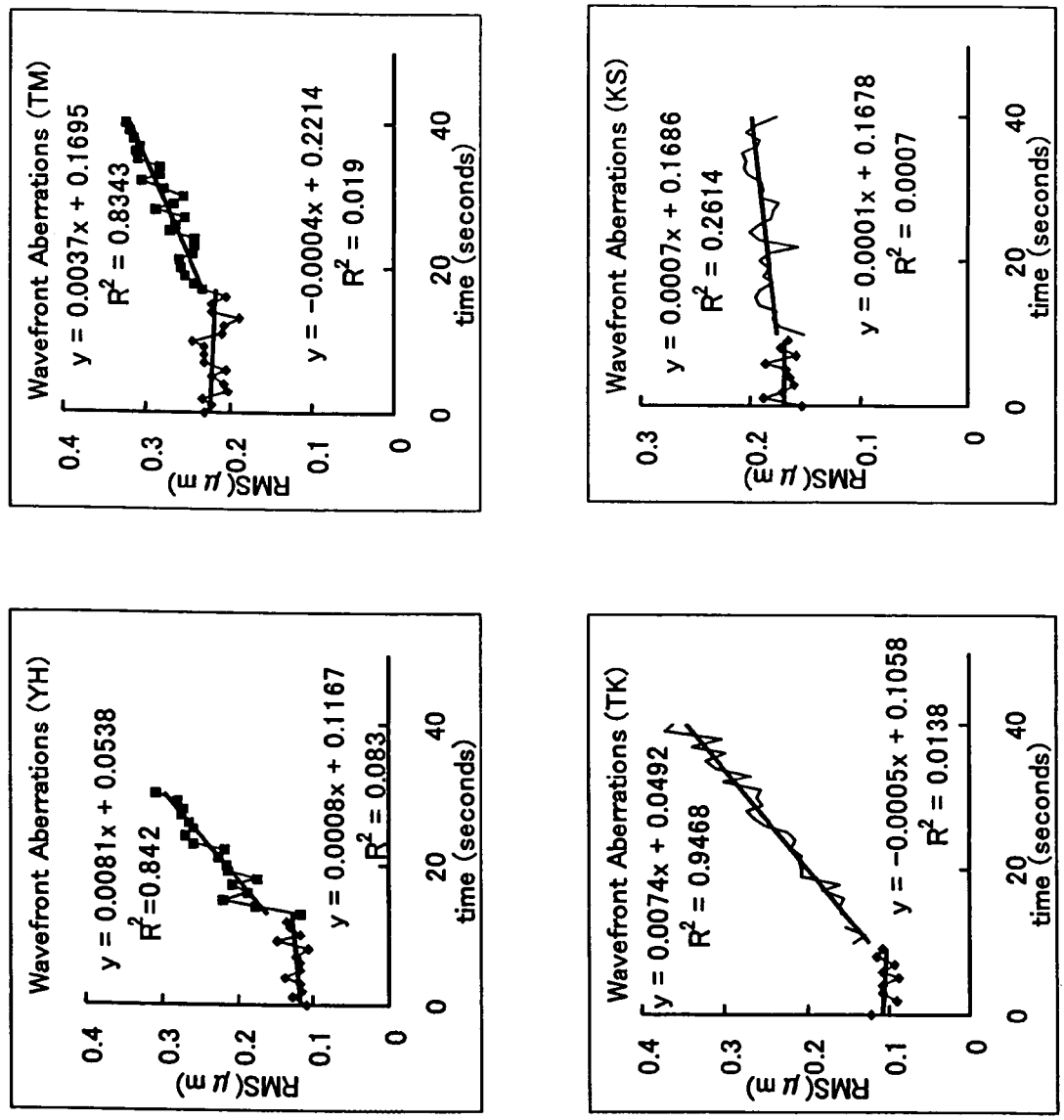
FIG. 15 is a view of a measurement example (2) of the breakup.

FIG. 15 shows a measurement example (2) of the breakup.

This drawing shows measurement examples of the breakup through the wavefront aberrations measured by using a Hartmann plate, and shows results in which the state of the breakup is measured for plural test subjects by the ophthalmologic apparatus of this embodiment. As shown in the drawing, the respective values of the breakup start time and the like can be obtained by regression lines.

Incidentally, similarly to the measurement example (1), as the alignment during the measurement, since the measurement is carried out for, for example, about 40 seconds, the auto alignment is preferable as the alignment. Besides, a mechanism may be provided in which an operator makes an alignment manually. Further, the degree of eye fatigue can also be measured by obtaining the number of times of blinking, or by performing a measurement as to whether a dry portion still exists though a tear film is recovered by a blink.

3-5. Measurement Flowchart of a Dry Eye (Second Embodiment)

Figure 16:
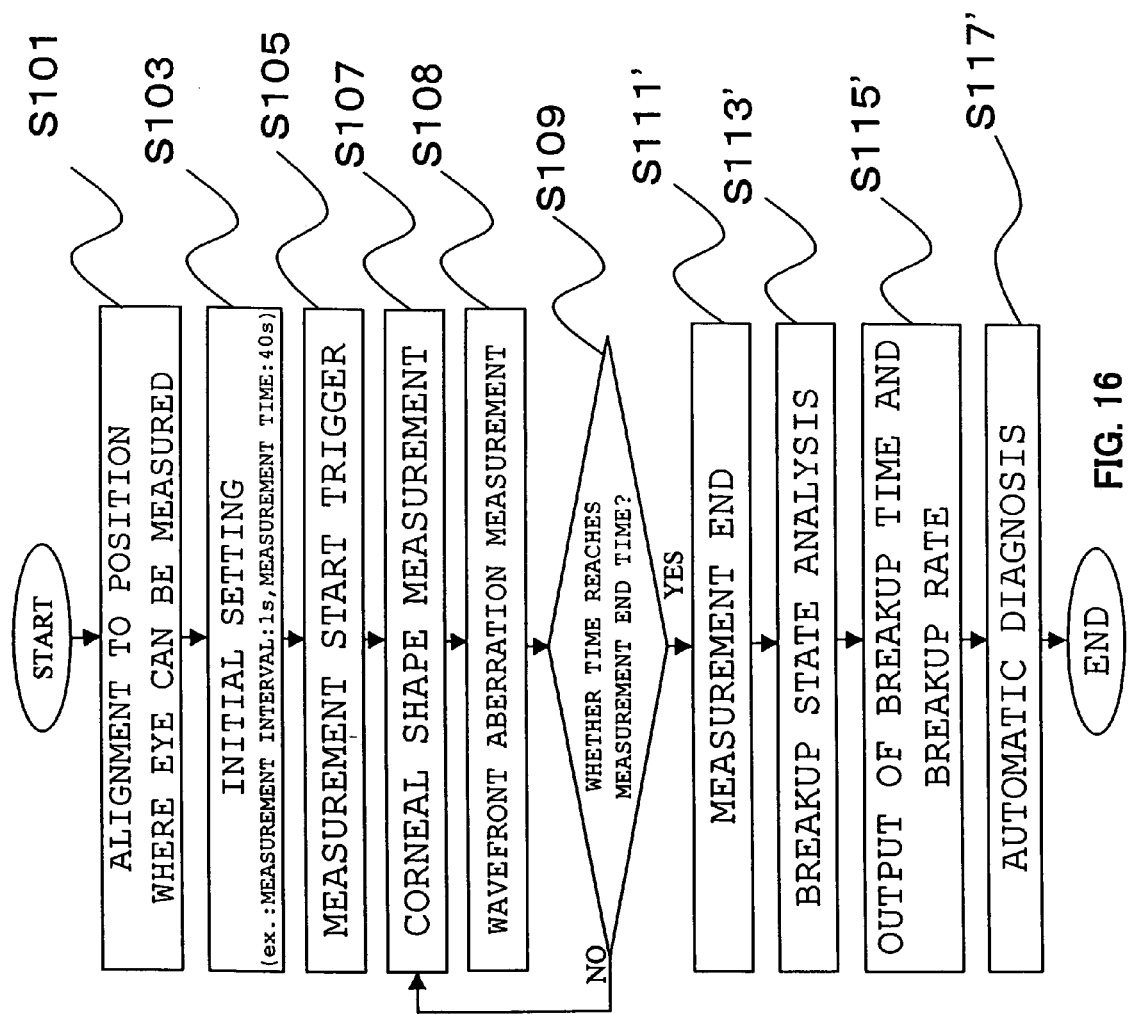
FIG. 16 is a flowchart of a dry eye according to a second embodiment.

FIG. 16 is a flowchart of a dry eye according to a second embodiment. This is such that a processing of a wavefront aberration measurement of step S108 is added to the flowchart of the first embodiment, and in the subsequent processing of respective steps S11' to S117', similar processing to the foregoing steps S111 to S117 is carried out on the basis of both aberrations (Zernike coefficients, etc.) measured at the corneal shape measurement (S107) and the wavefront aberration measurement (S108). Accordingly, as the output, both results can be displayed for comparison on the display part 700.

3-6. Example of Binocular Simultaneous Measurement

Figure 17:
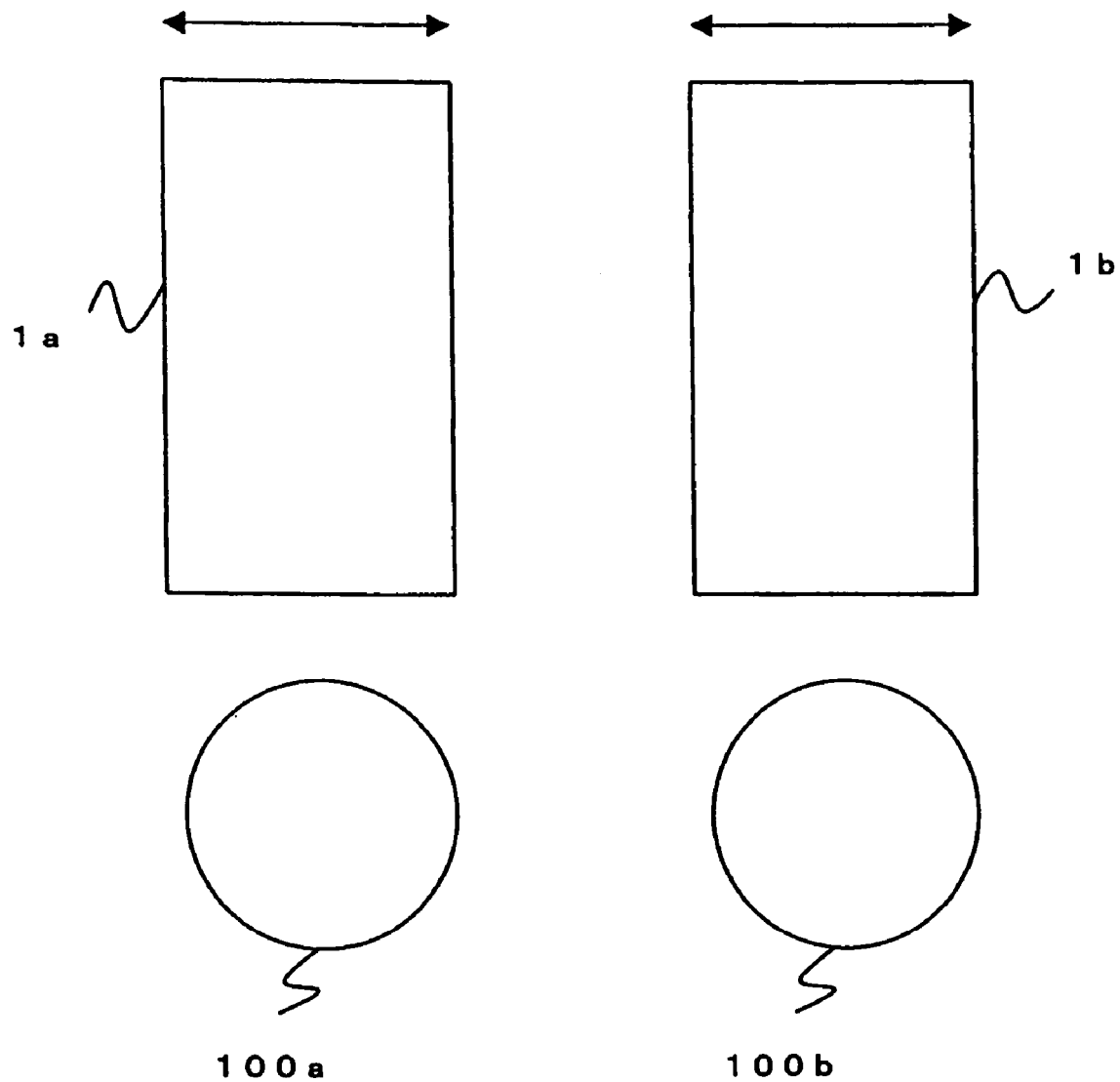
FIG. 17 is an ophthalmologic system structural view for a binocular simultaneous measurement.

FIG. 17 shows an ophthalmologic system structural view for a binocular simultaneous measurement. This ophthalmologic system includes optical systems 1a and 1b of FIG. 1 for both eyes 100a and 100b, and those can be independently adjusted and an alignment becomes possible for both the eyes. Then, although the description up to the above relates to a measurement for only one eye, a measurement can be made simultaneously for both the eyes by using the two apparatuses. Even in the case of a single eye measurement, both eyes must be opened, and a measurement of another single eye has not been capable of being performed for a while after the single eye measurement. However, in this case, there is a merit that the measurement can be certainly performed for both the eyes.

3-7. Measurement Flowchart of a Dry Eye (Third Embodiment)

Figure 22:
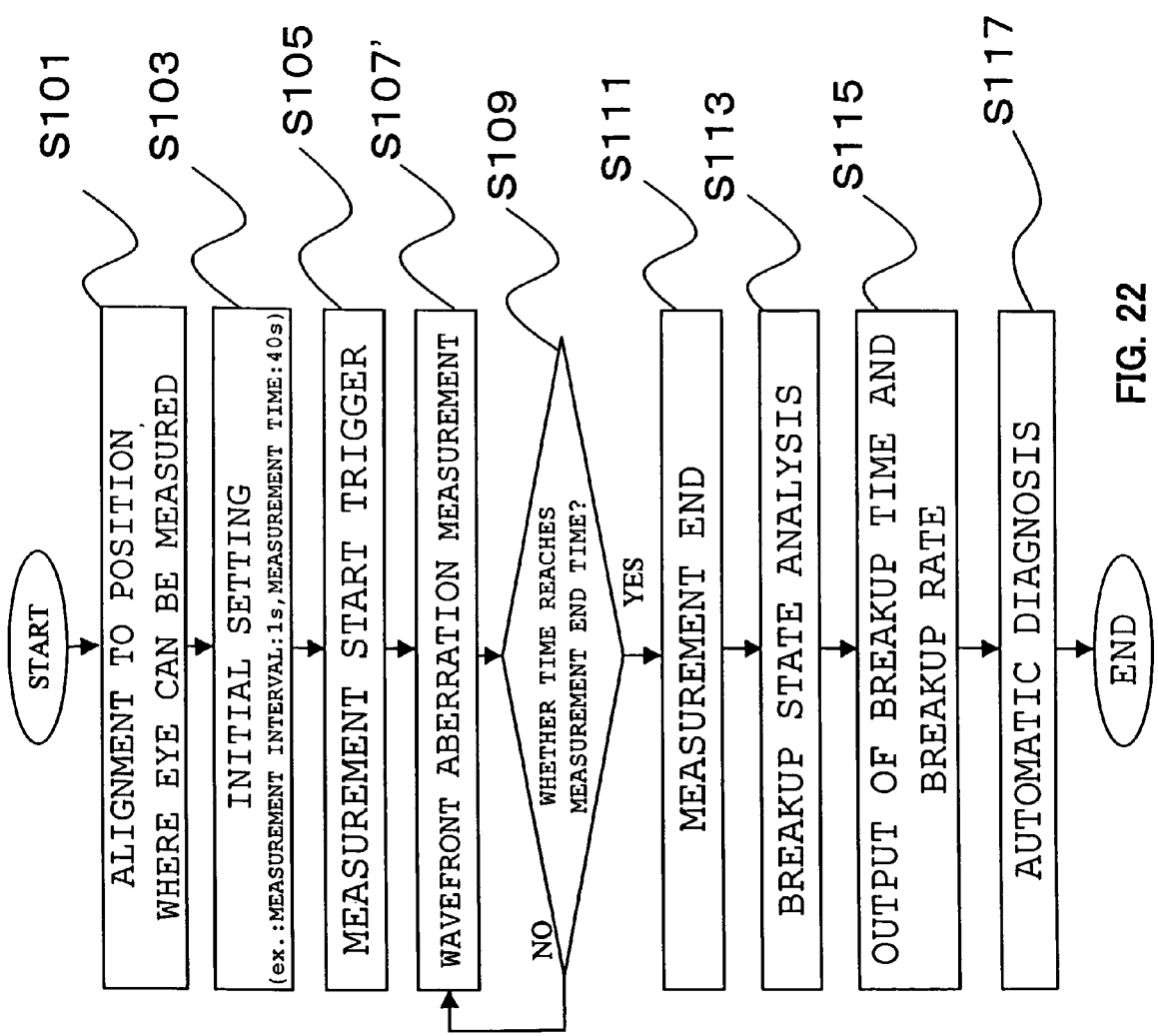
FIG. 22 is a flowchart of a dry eye according to a third embodiment.

FIG. 22 is a flowchart of a dry eye according to a third embodiment. This is such that instead of the step S107 of the flowchart of the first embodiment, the processing of a wavefront aberration measurement of step S107' is carried out, and in other steps S101 to S105 and S109 to S117, similar processing to the first embodiment is carried out. At the step S107', in accordance with a trigger, the measurement part (wavefront measurement part) 601 measures wavefront aberrations. Here, by the step S109, the arithmetic part 600 repeats the measurement of the wavefront aberrations by the measurement part (wavefront measurement part) 601 until time reaches a measurement end time.

4. Zernike Analysis and RMS

Next, a Zernike analysis will be described. A method of calculating Zernike coefficients $c_i^{2j-1}$ from generally known Zernike polynomials will be described. The Zernike coefficients $c_i^{2j-1}$ are important parameters for grasping the optical characteristics of the subject eye 100 on the basis of, for example, the inclination angle of the light flux obtained by the first light receiving part 21 through the Hartmann plate 22.

A wavefront aberration W(X, Y) of the subject eye 100 is expressed by a following expression using the Zernike coefficients $c_i^{2j-1}$ and Zernike polynomials $Z_i^{2j-1}$.

$$W(X, Y) = \sum_{i=0}^{n} \sum_{j=0}^{i} c_i^{2j-i} Z_i^{2j-i}(X, Y)$$

Where, (X, Y) are vertical and horizontal coordinates of the Hartmann plate 22.

Besides, with respect to the wavefront aberration W(X, Y), when the vertical and horizontal coordinates of the first light receiving part 21 are made (x, y), the distance between the Hartmann plate 22 and the first light receiving part 21 is made f, and the movement distance of a point image received by the first light receiving part 21 is made (Δx, Δy), the relation indicated by a following expression is established.

$$\frac{\partial W(X, Y)}{\partial X} = \frac{\Delta x}{f},$$
$$\frac{\partial W(X, Y)}{\partial Y} = \frac{\Delta y}{f}$$

Where, the Zernike polynomials $Z_i^{2j-1}$ is expressed by a following expression. Specifically, FIG. 18 is a view showing 10 the Zernike polynomials in the (r, t) coordinates, and FIG. 19 is a view showing the Zernike polynomials in the (x, y) coordinates.

$$Z_n^m = R_n^m(r) \left\{ \begin{matrix} \sin \\ \cos \end{matrix} \right\} \{m\theta\}$$

$m > 0$ sin
$m \leq 0$ cos $$R_n^m(r) = \sum_{S=0}^{(n-m)/2} (-1)^S \frac{(n-S)!}{S!\left\{\frac{1}{2}(n-m)-S\right\}!\left\{\frac{1}{2}(n+m)-S\right\}!} r^m$$

Incidentally, with respect to the Zernike coefficients $c_i^{2j-1}$ specific values can be obtained by minimizing the square error expressed by a following mathematical expression.

$$S(x) = \sum_{i=1}^{data\_number} \left[\left\{\frac{\partial W(X_i, Y_i)}{\partial X} - \frac{\Delta x_i}{f}\right\}^2 + \left\{\frac{\partial W(X_i, Y_i)}{\partial Y} - \frac{\Delta y_i}{f}\right\}^2\right]$$

Where, W(X, Y): wavefront aberration, (X, Y) Hartmann plate coordinates, (Δx, Δy): movement distance of the point image received by the first light receiving part 21, and f: distance between the Hartmann plate 22 and the first light receiving part 21.

The arithmetic part 600 calculates the Zernike coefficients $c_i^{2j-1}$ and obtains the optical characteristics, such as spherical aberrations, coma aberrations, and astigmatism by using these. Besides, the arithmetic part 600 calculates RMS of the aberration $RMS_i^{2j-1}$ by using the Zernike coefficients $c_i^{2j-1}$.

$$RMS_i^{2j-i} = \sqrt{\frac{\varepsilon_i^{2j-i}}{2(i+1)}} c_i^{2j-i}$$

$$(\varepsilon_i^{2j-i} = 2(2j = i), \varepsilon_i^{2j-i} = 1(2j \neq i))$$

5. Analysis of a Breakup State Using Higher Order Aberrations

The ophthalmologic apparatus of this embodiment can analyze the breakup state by using higher order aberrations of fifth order or higher.

In the case where the higher order aberrations of fifth order or higher are used as stated above, as the first conversion member 22, there is used one including a lens part of a short focal point and/or high density for changing part of the reflected light flux reflected and returned from the retina of the subject eye into at least substantially 21 beams. Besides, the measurement part 601 obtains aberration components of the subject eye including the higher order aberrations of at least fifth order from the received light signals of the first light receiving part 21 received plural times at the start point of time after the subject eye blinks and for the subsequent predetermined period. The judgment part 602 judges the state of the dry eye by comparing the temporal change of the higher order aberrations of fifth order or higher from the measurement results of the measurement part 601.

The breakup state analysis processing is similar to the respective flowcharts and ones explained in the description. However, the processing of setting that the higher order aberrations of fifth order or higher are used is carried out at a suitable timing. For example, at the step S103 of FIG. 3, this processing can be carried out by the setting previously set in the input part 650 or the memory 800. Further, two or more of the foregoing breakup measurement examples and the breakup measurement examples using the predetermined higher order aberrations are carried out, and they can be displayed on the display part 700.

Figure 20B:
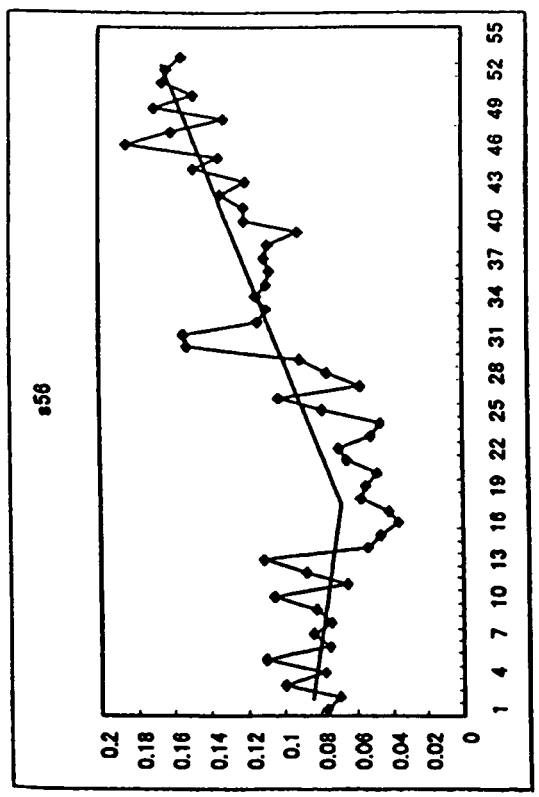
FIGS. 20A and 20B are views showing a measurement example of the breakup.
Figure 20A:
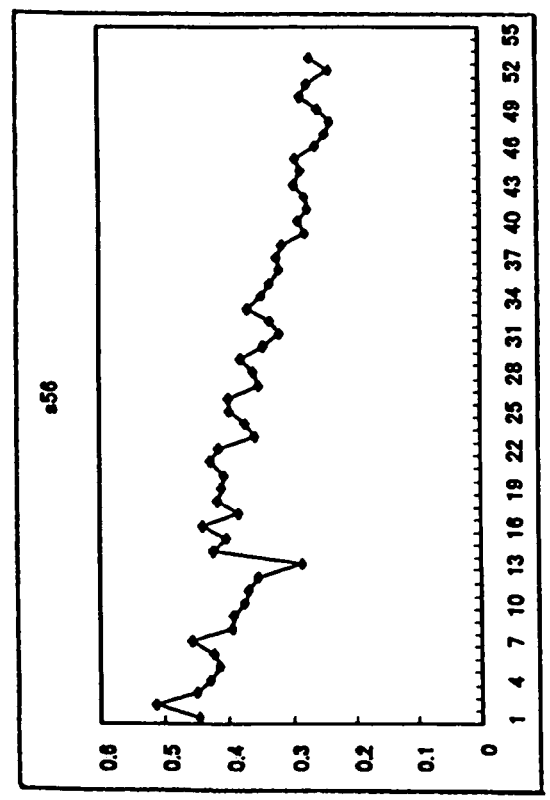

FIGS. 20A and 20B are views showing measurement examples of the breakup.

FIG. 20A shows the measurement example using the third or fourth order aberrations, and FIG. 20B shows the measurement example using the fifth or sixth order aberrations. As shown in the drawing, there is a case where the temporal change of the wavefront aberrations are influenced in the higher order aberrations of fifth order or higher more remarkably than the aberrations of fourth order or lower. In such a case, when the higher order aberrations are used, the breakup (division point) can be further clearly obtained.

Also with respect to the aberrations obtained by the corneal shape, a similar tendency can be recognized.

What is claimed is:

1. An ophthalmologic apparatus comprising:
   a first illuminating optical system for causing a measurement light flux with a specified shape to be incident on a cornea of a subject eye;
   a first light receiving optical system for receiving a reflected light from the cornea of the subject eye;
   a first light receiving part for changing a received reflected light from the first light receiving optical system into an electrical signal;
   a measurement part for obtaining a corneal shape of the subject eye from a received light signal of the first light receiving part plural times at a measurement start point of time and during a subsequent specified period; and
   a judgment part for judging a state of a dry eye by comparing temporal changes of the corneal shape from measurement results of the measurement part.

2. An ophthalmologic apparatus according to claim 1, further comprising:
   a second illuminating optical system for causing a measurement light flux to be incident on a retina of the subject eye;
   a second light receiving optical system for receiving a light through a conversion member for dividing a reflected light from the retina of the subject eye on which the measurement light flux is incident into many light fluxes; and
   a second light receiving part for converting a received reflected light received by the second light receiving optical system into an electrical signal,
   wherein
   the measurement part measures wavefront aberrations of the subject eye on the basis of divided light fluxes by the conversion member from a received light signal of the light receiving part during a specified period from a start point of time after the subject eye blinks, and
   the judgment part judges the state of the dry eye by comparing temporal changes of the measurement results on the basis of the corneal shape obtained by the measurement part and measurement results on the basis of the wavefront aberrations.

3. An ophthalmologic apparatus according to claim 1, wherein the measurement part determines a measurement period in accordance with the plural measurement results of the corneal shape.

4. An ophthalmologic apparatus according to claim 1, wherein in a case where a measurement period longer than the specified period is determined, the measurement part discontinues measurement within the specified period.

5. An ophthalmologic apparatus according to claim 1, wherein the state of the dry eye to be judged by the judgment part includes a breakup state.

6. An ophthalmologic apparatus according to claim 1, wherein the judgment part determines a function fitting to the measurement results, and obtains a value relating to a breakup for judgment of the state of the dry eye.

7. An ophthalmologic apparatus according to claim 6, wherein the value relating to the breakup includes one or plural of a breakup start time, a breakup speed, a breakup amount and a breakup rate.

8. An ophthalmologic apparatus according to claim 1, wherein
the judgment part further detects a blink, and
the measurement part performs a measurement of wavefront aberrations after a specified time has passed from the blink detected by the judgment part.

9. An ophthalmologic apparatus according to claim 8, wherein the judgment part detects the blink on the basis of an anterior eye part image.

10. An ophthalmologic apparatus according to claim 1, wherein a measurement is performed simultaneously for both eyes.

11. An ophthalmologic apparatus according to claim 1, wherein
the measurement part obtains aberration components of the subject eye including higher order aberrations of at least fifth order from the received light signal of the first light receiving part plural times at a start point of time after the subject eye blinks and during a subsequent specified period,
the judgment part judges a state of a dry eye by comparing temporal changes of the higher order aberrations of fifth order or higher from measurement results of the measurement part.

12. An ophthalmologic apparatus according to claim 2, wherein the conversion member converts the reflected light into at least substantially 21 beams.

13. An ophthalmologic apparatus comprising:
an illuminating optical system for causing a measurement light flux to be incident on a retina of a subject eye;
a light receiving optical system for receiving light through a conversion member for dividing a reflected light from the retina of the subject eye into many light fluxes;
a light receiving part for converting a received reflected light received by the light receiving optical system into an electrical signal;
a wavefront measurement part for obtaining aberration components of the subject eye including at least higher order aberrations from a received light signal of the light receiving part obtained plural times at a start point of time after a blink of the subject eye and during a subsequent specified period; and
a judgment part for judging a state of a dry eye by comparing temporal changes of at least the higher order aberrations of measurement results of the wavefront measurement part.

14. An ophthalmologic apparatus according to claim 13, wherein
the illuminating optical system illuminates a minute area on the retina of the subject eye with a light flux from a light source part for emitting a light flux with a first wavelength, and
the light receiving optical system receives light by the light receiving part through a first conversion member including a lens part having a high spatial resolution on a pupil and for converting part of a reflected light flux reflected and returned from the retina of the subject eye into at least substantially 17 beams.

15. An ophthalmologic apparatus according to claim 13, wherein
the light receiving optical system receives light through a conversion member for dividing the reflected light from the retina of the subject eye into many light fluxes,
the wavefront measurement part obtains aberration components of the subject eye including higher order aberrations of at least fifth order from a received light signal of the light receiving part plural times at a start point of time after a blink of the subject eye and during a subsequent specified period, and
the judgment part judges the state of the dry eye by comparing the temporal changes of the higher order aberrations of fifth order or higher from the measurement results of the wavefront aberration measurement part.

16. An ophthalmologic apparatus according to claim 15, wherein the first conversion member converts the reflected light into at least substantially 21 beams.

17. An ophthalmologic apparatus according to claim 15, wherein the wavefront measurement part determines a measurement period in accordance with the plural measurement results of wavefront aberrations.

18. An ophthalmologic apparatus according to claim 15, wherein in a case where the measurement period longer than the specified period is determined, the wavefront measurement part discontinues measurement within the specified period.

19. An ophthalmologic apparatus according to claim 15, wherein the state of the dry eye to be judged by the judgment part includes a breakup state.

20. An ophthalmologic apparatus according to claim 15, wherein the judgment part determines a function fitting to the measurement result, and obtains a value relating to a breakup for judgment of the state of the dry eye.

21. An ophthalmologic apparatus according to claim 20, wherein the value relating to the breakup includes one or plural of a breakup start time, a breakup speed, a breakup amount, and a breakup rate.

22. An ophthalmologic apparatus according to claim 15, wherein
the judgment part further detects a blink, and
the wavefront measurement part measures wavefront aberrations after a specified time has passed from the blink detected by the judgment part.

23. An ophthalmologic apparatus according to claim 22, wherein the judgment part detects the blink on the basis of an anterior eye part image.

24. An ophthalmologic apparatus according to claim 15, wherein wavefront aberrations measurement is simultaneously performed for both eyes.

* * * * *